(12) United States Patent
Driver

(10) Patent No.: US 8,980,972 B2
(45) Date of Patent: Mar. 17, 2015

(54) POLYMERISABLE MATERIAL

(75) Inventor: Michael Driver, Basingstoke (GB)

(73) Assignee: Vertellus Specialties Inc., Indianapolis, IN (US)

( * ) Notice: Subject to any disclaimer, the term of this patent is extended or adjusted under 35 U.S.C. 154(b) by 23 days.

(21) Appl. No.: 13/601,211

(22) Filed: Aug. 31, 2012

(65) Prior Publication Data

US 2013/0120708 A1 May 16, 2013

Related U.S. Application Data

(60) Provisional application No. 61/558,058, filed on Nov. 10, 2011.

(30) Foreign Application Priority Data

Nov. 10, 2011 (GB) .................................. 1119363.8

(51) Int. Cl.
| | | |
|---|---|---|
| G02B 1/04 | (2006.01) | |
| C08F 30/08 | (2006.01) | |
| A61F 2/14 | (2006.01) | |
| A61F 2/16 | (2006.01) | |
| C07F 9/10 | (2006.01) | |
| C08F 30/02 | (2006.01) | |

(52) U.S. Cl.
CPC ................. *C07F 9/106* (2013.01); *C08F 30/02* (2013.01); *G02B 1/043* (2013.01)
USPC ............................. 523/106; 523/107; 526/279

(58) Field of Classification Search
CPC ............ G02B 1/00; G02B 1/04; G02B 1/043; G02C 7/04; A61F 2/14; A61F 2/16
See application file for complete search history.

(56) References Cited

U.S. PATENT DOCUMENTS

| | | | |
|---|---|---|---|
| 3,808,178 A | | 4/1974 | Gaylord |
| 4,120,570 A | | 10/1978 | Gaylord |
| 4,136,250 A | | 1/1979 | Mueller et al. |
| 4,153,641 A | | 5/1979 | Deichert et al. |
| 4,417,066 A | * | 11/1983 | Westall .......................... 556/425 |
| 4,740,533 A | | 4/1988 | Su et al. |
| 5,034,461 A | | 7/1991 | Lai et al. |
| 5,070,215 A | | 12/1991 | Bambury et al. |
| 5,270,415 A | * | 12/1993 | Sulc et al. ....................... 526/265 |
| 5,648,442 A | * | 7/1997 | Bowers et al. .................. 526/277 |
| 6,090,901 A | * | 7/2000 | Bowers et al. .................. 526/277 |
| 6,200,626 B1 | * | 3/2001 | Grobe et al. ..................... 427/2.24 |
| 6,743,878 B2 | * | 6/2004 | Bowers et al. .................. 526/277 |
| 6,767,979 B1 | * | 7/2004 | Muir et al. ...................... 526/262 |
| 6,780,930 B2 | * | 8/2004 | Lewis et al. .................... 524/800 |
| 6,828,029 B1 | | 12/2004 | Lewis et al. |
| 2002/0165324 A1 | * | 11/2002 | Bowers et al. .............. 525/326.9 |
| 2003/0152786 A1 | * | 8/2003 | Lewis et al. .................... 428/447 |
| 2004/0208985 A1 | * | 10/2004 | Rowan et al. ................... 427/2.25 |
| 2004/0256232 A1 | | 12/2004 | Jiang et al. |
| 2006/0012751 A1 | * | 1/2006 | Rosenzweig et al. ...... 351/160 R |
| 2007/0099868 A1 | | 5/2007 | Harats et al. |
| 2007/0296914 A1 | | 12/2007 | Hong et al. |
| 2009/0130295 A1 | * | 5/2009 | Broguiere et al. ............... 427/58 |
| 2009/0304770 A1 | * | 12/2009 | Lewis et al. .................... 424/423 |
| 2010/0048515 A1 | | 2/2010 | Harats et al. |
| 2011/0319583 A1 | * | 12/2011 | Matsuoka et al. ............. 526/263 |

FOREIGN PATENT DOCUMENTS

| | | |
|---|---|---|
| DE | 1211156 | 2/1966 |
| EP | 0090539 | 11/1981 |
| EP | 0 537 972 | 4/1993 |
| EP | 0580435 | 1/1994 |
| EP | 0767212 | 4/1997 |
| EP | 0730599 | 4/2000 |
| EP | 1122258 | 8/2001 |
| EP | 2407493 A1 | 1/2012 |
| JP | 7 072430 | 3/1995 |
| JP | 2000169526 | 6/2000 |
| JP | 2000-186117 | 7/2000 |
| JP | 2007-09060 | 1/2007 |
| JP | 2007009060 | 1/2007 |
| WO | WO 92/07885 | 5/1992 |
| WO | WO 96/31566 | 10/1996 |
| WO | WO 2010055914 | 5/2010 |
| WO | WO 2010104000 | 9/2010 |
| WO | WO 2010/147779 | 12/2010 |
| WO | 2012045080 A1 | 4/2012 |
| WO | WO 2012/104349 | 8/2012 |

OTHER PUBLICATIONS

Thomson Scientific, London, GB; An 2007-180957, XP002686152, & JP 2007 009060 A (Nippon Oils & Fats Co Ltd) Jan. 18, 2007. (Abstract Only).

Lewis A L et al: "Crosslinkable coatings from phosphorylcholine-based polymers", Biomaterials, Elsevier Science Publishers BV., Barking, GB, vol. 22, No. 2, Jan. 15, 2001, pp. 99-111, XPO04236384.

Koinuma, Yasumi et al: "Diester monomer, its polymer, watercontaining soft contact", 1994, XP002687478. (Abstract Only).

Suzuki, Hiroshi et al: "Preparation of polymerizable phosphorylcholine derivatives with medical applications", 1995, XP002687479. (Abstract Only).

Nakabayashi, Nobuo et al: "Low-toxicity aqueous solution of phosphorylcholine group-bearing Polymer and its manufacture", 1996, XP002687480. (Abstract Only).

Harats, Dror et al: "Oxidized lipids and uses thereof in the treatment of inflammatory diseases and disorders", 2010, XP002687481. (Abstract Only).

(Continued)

*Primary Examiner* — Robert S Loewe

(74) *Attorney, Agent, or Firm* — Barnes & Thornburg LLP

(57) ABSTRACT

Polymerisable material which comprises a polymerisable group, a siloxane group-containing component and a zwitterionic group is described. The polymerisable material may be used to produce polymers and articles, in particular contact lenses.

31 Claims, No Drawings

(56) References Cited

OTHER PUBLICATIONS

Harats, Dror et al: "Oxidized lipids and uses thereof in the treatment of inflammatory diseases and disorders", 2007, XP002687482. (Abstract Only).
Ol'dekop, Y: "XRN 3984136", XP55044654,accession No. XRN 3984136 Database accession No. XRN 3984136; & Y Ol'dekop: "REAXYS XRN=3984136", Zhurnal Organicheskoi Khimii, vol. 15, No. 1, Jan. 1, 1979, pp. 39-50, XP055044654.
Raghavan S et al: "A novel, easy and mild preparation of sulfilimines from sulfoxides using the Burgess reagent", Tetrahedron Letters, Elsevier, Amsterdam, NL, vol. 49, No. 27, Jun. 30, 2008 pp. 4256-4259.XP022695656.
Kita, Noriyasu et al: "Imidazole derivative and silver halide photographic material spectrally sensitized with the compound", 1997, XP002687483. (Abstract Only).
Anton P et al: "Synthesis of polymeric surfactants by radical thiol/en addition reaction", European Polymer Journal, Pergamon Press Ltd. Oxford, GB, vol. 31, No. 4, Apr. 1, 1995, pp. 387-394.
Koberle and A Laschewsky P: "Hydrophobically Modified Zwitterionic Polymers: Synthesis, Bulk Properties, and Miscibility with Inorganic Salts". Macromolecules, American Chemical Society,Washington, DC; US,vol. 27, Jan. 1, 1994, pp. 2165-2173.
Kupetis, G. et al: "Unsaturated compounds of a pyridine series. (2. Synthesis of sulfobetaines of unsaturated esters of nicotinic acid)", 1985, XP002687484. (Abstract Only).
Emerson Poley Peqanha et al: "Synthesis and pharmacological evaluation of a new class of bicyclic phospholipids, designed as platelet activating factor antagonists", Il Farmaco, vol. 53, No. 5, May 1, 1998, pp. 327-336.
Bayer A.G.: "XRN 4028356", XP002687591,accession No. XRN 4028356 Database accession No. XRN 4028356 ; & DE 12 11 156 B (Bayer AG) Feb. 24, 1966.
Sato, Toshihiro et al: "Ammonium phosphate-containing polymers, lenses using them, and their manufacture", 2000, XP002687477. (Abstract Only).
Nakayama, Takafumi et al: "Presensitized lithographic plates and ethylenic polymers with betaine structures for them", XP002687485, retrieved from STN Database accession No. 2012:338275, abstract.
Bowen, Martina E. et al: "Aqueous fire-fighting foams with reduced fluorine content", (Apr. 5, 2012), XP002687486. (Abstract Only).
Lewis, Andrew L. "Phosphorylcholine-based polymers and their use in the prevention of biofouling." *Colloids and Surfaces B: Biointerfaces* 18.3 (2000): 261-275.
Guillon, Jean-Pierre, Judith Morris, and Brenda Hall. "Evaluation of the pre-lens tear film forming on three disposable contact lenses." *Lacrimal Gland, Tear Film, and Dry Eye Syndromes 3*. Springer US, 2002. 901-915.
Umeda, Takashi, Tadao Nakaya, and Minoru Imoto. "Polymeric phospholipid analogues, 14. The convenient preparation of a vinyl monomer containing a phospholipid analogue." *Die Makromolekulare Chemie, Rapid Communications 3.7* (1982): 457-459.
Thuong, NT; Chabrier, P. Nouvelle Methode de Preparation de la Phosphorylcholine, de la Phosohoraylhomo-choline et de leura WrivBs. Bull. Chem. Soc. Fr. 1974, 667-671.
Machine-generated English-language translation of JP-2000-169526, translation generated Mar. 2014, 16 pages.
Machine-generated English-language translation of WO-2010055914, translation generated Mar. 2014, 25 pages.
International Search Report for PCT US2012 053372.
International Search Report for PCT US2012 053370.
International Search Report for PCT US20120 53373.
Suzuki, EPO Abstract of JP 2007-9060.

\* cited by examiner

POLYMERISABLE MATERIAL

CROSS-REFERENCE TO RELATED APPLICATIONS

This application claims the benefit of U.S. Provisional Application No. 61/558,058, filed Nov. 10, 2011, under 35 U.S.C. §119(e), and UK Application No. 1119363.8, filed on Nov. 10, 2011, under 35 U.S.C. §119(a), the disclosures of each of which are incorporated by reference herein in their entireties.

This invention relates to new polymerisable materials, methods for producing polymers, polymers and articles formed therefrom. The polymerisable materials of the present invention are useful in the manufacture of products in which an appropriate combination of gas permeability and hydrophilicity is required. These include ophthalmic devices, such as contact lenses and membranes and films used in wound dressings and sensor systems, for example.

Silicone hydrogels have found utility in medical device applications where gas permeability is desirable. The siloxane component makes the major contribution to gas permeability in such systems. In certain applications, for example, contact lenses, it is advantageous for this property to be combined with a high surface energy to provide an easily wettable and dehydration-resistant material so that the resulting lens is comfortable on the wearer's eye, especially for extended wear periods.

The silicone components used in the production of silicone hydrogels are inherently hydrophobic and, in order to provide acceptable levels of wettability, they are typically combined with hydrophilic co-monomers. The process of combining a hydrophilic component with an inherently hydrophobic material is not always straightforward due to solubility incompatibilities between the two components and, as a consequence, it is often necessary to employ the use of diluents. The diluent may comprise other polymerisable co-monomers, macromere, or non-reactive solvents, or combinations thereof. Despite the use of these techniques, the resulting materials may still have unsuitable mechanical properties (too stiff, too flexible, prone to breakage), poor wettability (leading to discomfort on-eye), poor resistance to dehydration (leading to changes in lens dimensions and break-up of the tear film), poor optical properties (materials may be hazy or opaque) and poor biocompatibility (leading to deposition of tear film components such as lipids and proteins). Indeed, the most significant challenge in this field is to provide materials with an appropriate combination of all of these properties.

The inclusion of hydrophilic, zwitterionic components, such as phosphorylcholine, into polymer structures has been shown to produce materials with improved biocompatibility, resistance to dehydration and improved on-eye comfort. An example of such a material is 2-(methacryloyloxyethyl)-2'-(trimethylammoniummethyl)phosphate, inner salt (MPC). However, practical difficulties may be encountered when attempting to combine these polar zwitterionic materials which are often solids, with silicone components, because they have little or no solubility in silicone systems. It has been found that, even when a suitable mixture of siloxane, solubilising co-monomer and zwitterionic monomer proves capable of providing a single phase solution, the resulting polymer may prove to be opaque as a result of phase separation and thereby be unsuitable for use in an ophthalmic device.

Furthermore, lens materials made using water-insoluble monomers have to be subjected to an organic solvent extraction step as part of the manufacturing process to remove residual unreacted monomers and unincorporated, low molecular weight species. This is necessary to avoid potential ocular damage to the end wearers of the contact lens. In this regard, the lens, swollen in solvent, then has to be treated with a suitable aqueous composition, such as a buffered saline, to ensure that there is no appreciable amount of residual solvent left in the lens. These steps add to the complexity of the manufacturing process and generate additional waste streams.

Accordingly, there is a need for new materials which are clear and which combine gas permeability with a resistance to dehydration and provide good wettability, thus making it possible to produce polymers useful for forming ophthalmic devices, in particular contact lenses with beneficial properties.

Against this background, the present invention provides new polymerisable materials which combine both a zwitterionic functionality and a siloxane functionality into the same molecule.

Thus, in a first aspect, the present invention provides a polymerisable material of formula (I) or (II):

$$(X-Y^1)_m-W(Y^2-Z)_n \quad (I)$$

$$[(X)_m-Y^3(Z)_p]_v-W-R^1 \quad (II)$$

wherein

X is a polymerisable group;

$Y^1$ and $Y^2$ are each independently a linker group selected from the group consisting of a bond, $C_{1-12}$ alkylene, $C_{2-12}$ alkenylene, $C_{2-12}$ alkynylene, $C_{3-12}$ cycloalkylene, $C_{3-12}$ cycloalkenylene, $C_{2-12}$ heteroalkenylene, $C_{2-12}$ heteroalkynylene, arylene, heteroarylene, —C(O)—$C_{1-12}$ alkylene, —C(S)—$C_{1-12}$ alkylene, —C(O)O—$C_{1-12}$ alkylene, —C(O)S—$C_{1-12}$ alkylene, —C(O)N($R^M$)—$C_{1-12}$ alkylene, —C(S)—$C_{1-12}$ alkylene, —C(S)O—$C_{1-12}$ alkylene, —C(S)S—$C_{1-12}$ alkylene, —C(S)N($R^M$)—$C_{1-12}$ alkylene, —(CH$_2$)$_q$(OCH$_2$CH$_2$)$_r$— and —(CH$_2$CH$_2$O)$_r$(CH$_2$)$_q$—, wherein $R^M$ is hydrogen or $C_{1-4}$ alkyl, q is an integer from 1 to 10, r is an integer from 1 to 10, wherein one or more carbon atoms in the $C_{1-12}$ alkylene group may be optionally replaced with a heteroatom selected from the group consisting of S and O and the alkylene, alkenylene, alkynylene, cycloalkylene, cycloalkenylene, heteroalkenylene, heteroalkynylene, arylene and heteroarylene groups may be optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)—C(O)—($C_1$-$C_{10}$ alkyl), —NH—S(O)$_2$—($C_1$-$C_{10}$ alkyl), —NH—($C_1$-$C_{10}$ alkyl)-S (O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O;

$Y^3$ is a linker group;

$R^1$ is a $C_{1-12}$ alkyl group which may be optionally substituted with one or more $R^N$;

W is a siloxane group-containing component;

Z is a zwitterionic group;

m is an integer from 1 to 10;

n is an integer from 1 to 3;
p is an integer from 1 to 3; and
v is an integer from 1 to 3.

By incorporating both a polar, zwitterionic functionality and a siloxane functionality into the same molecule, the polymerisable materials of the present invention provide a means for making clear, gas permeable materials with a resistance to dehydration and tear film deposits, in combination with good wettability for on-eye comfort. Advantageously, any phase separation in the polymerisable materials of the present invention may be at a molecular level and so will not be visible to the naked eye. Furthermore, because the functionalities are combined on a molecular level rather than by combining different co-monomers, it is possible to provide materials which have a higher oxygen permeability than might be expected for a given water content. A further advantage of the polymerisable siloxane materials of the present invention is that they may be water soluble which would have the effect of simplifying manufacturing processes and reducing waste streams.

The polymerisable material of the present invention includes a polymerisable group, siloxane functionality and a zwitterionic functionality within the same molecule.

Although formula (I) and formula (II) (and the chemical formulae which follow herein) are represented without any indication of specific stereochemistry, the skilled person will understand that a number of isomers are possible. In this regard, the present invention includes within its scope, all possible stereoisomers of the chemical structures depicted.

The polymerisable group X is not limited and it may be any group which is capable of reaction under polymerisation conditions to form a polymer. It is the presence of the polymerisable group in the materials of the present invention which means that it is possible to form polymers and, ultimately, contact lenses from the materials of the present invention. In certain embodiments, the polymerisable group includes at least one carbon-carbon unsaturated bond. In such embodiments, the group is capable of addition polymerisation reactions. Alternatively, or in addition, the group which is capable of reaction to form a polymer is a multi-functionalised derivative which is capable of condensation polymerisation. This includes, for example, materials such as diols, diamines, diacids and derivatives thereof.

In one embodiment, the polymerisable material of the present invention is a material of formula (I). In an alternative embodiment, the polymerisable material of the present invention is a material of formula (II).

In one embodiment, the polymerisable group X includes a group which is selected from the group consisting of acrylates, methacrylates, acrylamides, methacrylamides, styrenic and vinylic groups. Examples of suitable vinylic groups include allyl derivatives, N-vinyl lactam derivatives, such as suitably substituted N-vinyl pyrrolidone derivatives and N- and O-vinyl derivatives.

In one embodiment, the polymerisable group X is a methacrylate or acrylate group. Preferably, the polymerisable group X is a methacrylate group.

With reference to formula (I) and formula (II) above, m is an integer which defines the number of polymerisable groups, X, present in the polymerisable material. m may be 1, 2, 3, 4, 5, 6, 7, 8, 9 or 10. Preferably, m is 1 or 2.

$Y^1$ is a linker group which forms a link between the polymerisable group X and the siloxane group-containing component, W, in a polymerisable material of formula (I). $Y^2$ is a linker group which forms a link between the siloxane group-containing component, W and the zwitterionic group, Z in a polymerisable material of formula (I). $Y^1$ and $Y^2$ are each independently selected from the group consisting of a bond, $C_{1-12}$ alkylene, $C_{2-12}$ alkenylene, $C_{2-12}$ alkynylene, $C_{3-12}$ cycloalkylene, $C_{3-12}$ cycloalkenylene, $C_{2-12}$ heteroalkenylene, $C_{2-12}$ heteroalkynylene, arylene, heteroarylene, —C(O)—$C_{1-12}$ alkylene, —C(S)—$C_{1-12}$ alkylene, —C(O)O—$C_{1-12}$ alkylene, —C(O)S—$C_{1-12}$ alkylene, —C(O)N($R^M$)—$C_{1-12}$ alkylene, —C(S)—$C_{1-12}$ alkylene, —C(S)O—$C_{1-12}$ alkylene, —C(S)S—$C_{1-12}$ alkylene, —C(S)N($R^M$)—$C_{1-12}$ alkylene, —(CH$_2$)$_q$(OCH$_2$CH$_2$)$_r$— and —(CH$_2$CH$_2$O)$_r$(CH$_2$)$_q$—, wherein $R^M$ is hydrogen or $C_{1-4}$ alkyl, q is an integer from 1 to 10, r is an integer from 1 to 10, wherein one or more carbon atoms in the $C_{1-12}$ alkylene group may be optionally replaced with a heteroatom selected from the group consisting of S and O and the alkylene, alkenylene, alkynylene, cycloalkylene, cycloalkenylene, heteroalkenylene, heteroalkynylene, arylene and heteroarylene groups may be optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)—S(O)$_2$—($C_1$-$C_{10}$ alkyl), —(C$_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and ═O. $Y^1$ and $Y^2$ may be the same or different. In one embodiment, $Y^1$ and $Y^2$ are the same. In an alternative embodiment, $Y^1$ and $Y^2$ are different.

In one embodiment, $Y^1$ and $Y^2$ are each independently a $C_{1-12}$ alkylene group. In an alternative embodiment, $Y^1$ is a group of formula —(CH$_2$)$_q$(OCH$_2$CH$_2$)$_r$— and $Y^2$ is a group of formula —(CH$_2$CH$_2$O)$_r$(CH$_2$)$_q$—, wherein r is an integer in the range from 1 to 10, preferably 4 to 6 and q is an integer in the range from 1 to 10, in one embodiment, 2 to 4, preferably 3.

$Y^3$ is a linker group which forms a link between the polymerisable group, X and the siloxane group, W, in polymerisable material of formula (II). In this embodiment of the present invention, the zwitterionic group, Z, is a substituent on the linker group, $Y^3$. The nature of $Y^3$ is not particularly limited and in a preferred embodiment, $Y^3$ is selected from the group consisting of a bond, $C_{1-12}$ alkylene, $C_{2-12}$ alkenylene, $C_{2-12}$ alkynylene, $C_{3-12}$ cycloalkylene, $C_{3-12}$ cycloalkenylene, $C_{1-12}$ heteroalkylene, $C_{2-12}$ heteroalkenylene, $C_{2-12}$ heteroalkynylene, arylene, heteroarylene, —C(O)—, —C(S)—, —C(O)O—, —C(O)S—, —C(O)N($R^M$)—, —C(S)—, —C(S)O—, —C(S)S— and —C(S)N($R^M$)—, wherein $R^M$ is hydrogen or $C_{1-4}$ alkyl. The alkylene, alkenylene, alkynylene, cycloalkylene, cycloalkenylene, heteroalkylene, heteroalkenylene, heteroalkynylene, arylene and heteroarylene groups may be optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —(C$_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—

($C_1$-$C_{10}$ alkyl), —S(O)$_2$—N($C_1$-$C_{10}$ alkyl)$_2$ and =O. The position of the group Z as a substituent of the linker group Y$^3$ is not limited. In this regard, the group Z may be a substituent on any one of the carbon atoms which form a part of the backbone of the linker group, Y$^3$.

In one embodiment, Y$^3$ is a $C_{1\text{-}12}$ alkylene or heteroalkylene group, in particular a heteroalkylene group of formula —(CH$_2$)$_q$(OCH$_2$CH$_2$)$_r$— or —(CH$_2$CH$_2$O)$_r$(CH$_2$)$_q$—, wherein q is an integer from 1 to 10 and r is an integer from 1 to 10. In a preferred embodiment, Y$^3$ is —(CH$_2$)$_3$—O—(CH$_2$)$_3$—. In a preferred embodiment of the present invention, the position of substitution of the Z group on the Y$^3$ group is such that the group —Y$^3$(Z)— is —(CH$_2$CH(Z)CH$_2$)—O—(CH$_2$)$_3$—.

W is a siloxane group-containing component. It is the inclusion of the siloxane functionality in the polymerisable material of the present invention which provides a material which has good gas permeability. The nature of the siloxane group-containing component is not particularly limited and the skilled person will be familiar with suitable components. A siloxane group is one which includes the residue having the general structure —[Si(R)$_2$O]—, wherein each R is independently selected from hydrogen or a $C_{1\text{-}12}$ alkylene, $C_{2\text{-}12}$ alkenylene, $C_{2\text{-}}$ alkynylene, $C_{3\text{-}12}$ cycloalkylene, $C_{3\text{-}12}$ cycloalkenylene, $C_{1\text{-}12}$ heteroalkylene, $C_{2\text{-}12}$ heteroalkenylene, $C_{2\text{-}12}$ heteroalkynylene, arylene, heteroarylene group, optionally substituted with one or more R$^N$, wherein each R$^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)—S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O. The R groups may be the same or different. In one embodiment all of the R groups are the same. In an alternative embodiment, the R groups are different. Preferably R is a $C_{1\text{-}12}$ alkylene group, preferably a $C_{1\text{-}6}$ alkylene group. Preferably, the Si and attached O are present in the siloxane group in an amount greater than 20 weight percent, and more preferably greater than 30 weight percent of the total molecular weight of the siloxane group-containing component.

In one embodiment, the siloxane group-containing component has the formula (IIIA):

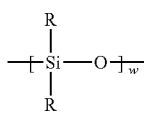

(IIIA)

wherein R is as defined previously and w is an integer from 1 to 500.

In one embodiment, the siloxane group-containing component has the formula (IIIB):

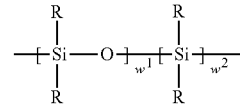

(IIIB)

wherein R is as defined previously and w$^1$ and w$^2$ are independently an integer in the range from 1 to 500.

In one embodiment, the siloxane group-containing component has the formula (IIIC):

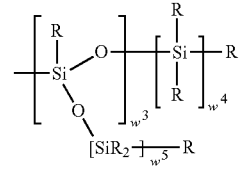

(IIIC)

wherein R is as defined previously and w$^3$, w$^4$ and w$^5$ are each independently an integer in the range from 1 to 500.

In one embodiment, the siloxane group-containing component has the formula (IIID):

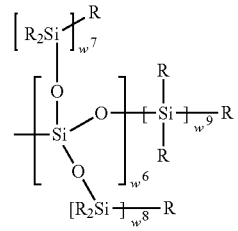

(IIID)

wherein R is as defined previously and w$^6$, w$^7$, w$^8$ and w$^9$ are each independently an integer in the range from 1 to 500.

Z is a zwitterionic group. Where the polymerisable material has formula (I), Z is bonded to Y$^2$. Where the polymerisable material has formula (II), Z is a substituent on the linker group Y$^3$. A zwitterionic group is one which carries both a positive charge and a negative charge located on different atoms within the group such that the net charge of the group is zero. As a consequence, zwitterionic groups have a high polarity and a natural affinity for water. Phospholipids, such as phosphatidylcholine and sphingomyelin, which are the major components of the outer membrane of all living cells have a zwitterionic structure. Hence, the zwitterionic monomers can be used to produce polymers which mimic the zwitterionic structure of phospholipids. This results in the biocompatibility of the polymers which may be produced. The presence of the zwitterionic functionality in the polymerisable material of the present invention means that the resulting polymer shows good resistance to dehydration and a good wettability, both of which are important for comfort where the polymer is to be used to form a contact lens.

In one embodiment, Z is a zwitterionic group selected from the group consisting of formula (IVA), (IVB), (IVC), (IVD) and (IVE).

Preferably, Z is a zwitterionic group of formula (IVB).

Group (IVA) has the formula:

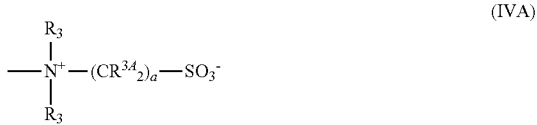
(IVA)

wherein each $R^3$ and $R^{3A}$ is independently selected from hydrogen and $C_{1-4}$ alkyl and a is an integer from 2 to 4.

In one embodiment, both $R^3$ groups are the same. In particular, both $R^3$ groups may be $C_{1-4}$ alkyl, in one embodiment, methyl.

In one embodiment, both $R^{3A}$ groups are the same. In particular, both $R^{3A}$ groups may be hydrogen.

In one embodiment, a is 2 or 3. In a further embodiment, a is 3.

In one embodiment where Z is a group of formula (IVA), m is 1 or 2.

Group (IVB) has the formula:

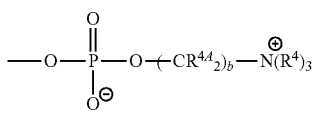
(IVB)

wherein each $R^4$ and $R^{4A}$ is independently selected from hydrogen and $C_{1-4}$ alkyl and b is an integer from 1 to 4;

In one embodiment, all $R^4$ groups are the same. In particular, all $R^4$ groups may be $C_{1-4}$ alkyl, in one embodiment, methyl. In one embodiment, at least one $R^4$ group is $C_{1-4}$ alkyl.

In one embodiment, the $R^{4A}$ groups are the same. In particular, the $R^{4A}$ groups may be hydrogen.

In one embodiment, b is 2 or 3. In a further embodiment, b is 2.

In one embodiment where Z is a group of formula (IVB), m in formula (I) is 1 or 2.

In one embodiment, preferably Z is a group of formula (IVB), wherein all $R^4$ groups are methyl groups and b is 2. In this embodiment, Z is a phosphorylcholine (PC) group. PC groups occur naturally in the phospholipids which form the membranes of all living cells. Therefore, with a view to mimicking the zwitterionic properties of phospholipids, it is particularly advantageous for Z to be a PC group.

Group (IVC) has the formula:

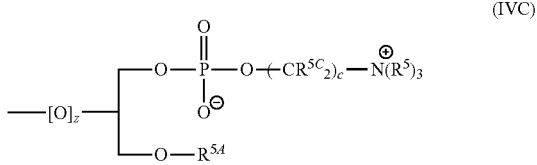
(IVC)

wherein each $R^5$ and $R^{5C}$ is independently selected from hydrogen and $C_{1-4}$ alkyl; $R^{5A}$ is hydrogen or a group —C(O)$B^1R^{5B}$, wherein $R^{5B}$ is hydrogen or methyl, $B^1$ is selected from the group consisting of a bond; $C_{1-10}$ alkylene, $C_{2-10}$ alkenylene, $C_{2-10}$ alkynylene, $C_{3-10}$ cycloalkylene, $C_{3-10}$ cycloalkenylene, $C_{1-10}$ heteroalkylene, $C_{2-10}$ heteroalkenylene, $C_{2-10}$ heteroalkynylene, arylene, heteroarylene, wherein the alkylene, alkenylene, alkynylene, cycloalkylene, cycloalkenylene, heteroalkylene, heteroalkenylene, heteroalkynylene, arylene and heteroarylene groups may be optionally substituted with one or more $R^N$ as defined previously, and c is an integer from 1 to 4, wherein if Z is directly bonded to an O or N atom, z is 0 and otherwise z is 1.

In one embodiment, the $R^5$ groups are the same. In particular, the $R^5$ groups may be $C_{1-4}$ alkyl, in one embodiment, methyl. In one embodiment, at least one $R^5$ group is $C_{1-4}$ alkyl.

In one embodiment, both $R^{5C}$ groups are the same. In particular, the $R^{5C}$ groups may be hydrogen.

In one embodiment, c is 2 or 3. In a further embodiment, c is 3.

Group (IVD) has the formula:

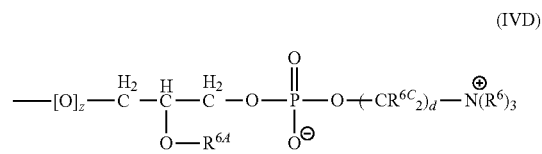
(IVD)

wherein each $R^6$ and $R^{6C}$ is independently selected from hydrogen and $C_{1-4}$ alkyl; $R^{6A}$ is hydrogen or a group —C(O)$B^2R^{6B}$, wherein $R^{6B}$ is hydrogen or methyl, $B^2$ is selected from the group consisting of a bond; $C_{1-10}$ alkylene, $C_{2-10}$ alkenylene, $C_{2-10}$ alkynylene, $C_{3-10}$ cycloalkylene, $C_{3-10}$ cycloalkenylene, $C_{1-10}$ heteroalkylene, $C_{2-10}$ heteroalkenylene, $C_{2-10}$ heteroalkynylene, arylene, heteroarylene, wherein the alkylene, alkenylene, alkynylene, cycloalkylene, cycloalkenylene, heteroalkylene, heteroalkenylene, heteroalkynylene, arylene and heteroarylene groups may be optionally substituted with one or more $R^N$ as defined previously, and d is an integer from 1 to 4, wherein if Z is directly bonded to an O or N atom, z is 0 and otherwise z is 1;

In one embodiment, the $R^6$ groups are the same. In particular, the $R^6$ groups may be $C_{1-4}$ alkyl, in one embodiment, methyl. In one embodiment, at least one $R^6$ group is $C_{1-4}$ alkyl.

In one embodiment, both $R^{6C}$ groups are the same. In particular, the $R^{6C}$ groups may be hydrogen.

In one embodiment, d is 1 or 2. In a further embodiment, d is 2.

Group (IVE) has the formula:

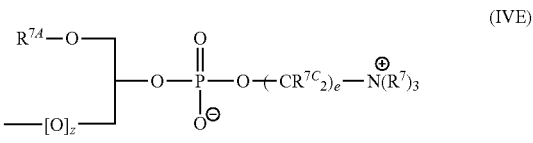
(IVE)

wherein each $R^7$ and $R^{7C}$ is independently selected from hydrogen and $C_{1-4}$ alkyl; $R^{7A}$ is hydrogen or a group —C(O)$B^2R^{7B}$, wherein $R^{7B}$ is hydrogen or methyl, $B^2$ is selected from the group consisting of a bond; $C_{1-10}$ alkylene, $C_{2-10}$ alkenylene, $C_{2-10}$ alkynylene, $C_{3-10}$ cycloalkylene, $C_{3-10}$ cycloalkenylene, $C_{1-10}$ heteroalkylene, $C_{2-10}$ heteroalkenylene, $C_{2-10}$ heteroalkynylene, arylene, heteroarylene, wherein the alkylene, alkenylene, alkynylene, cycloalkylene, cycloalkenylene, heteroalkylene, heteroalkenylene, heteroalkynylene, arylene and heteroarylene groups may be optionally substituted with one or more $R^N$ as defined previously, and e is an integer from 1 to 4, wherein if Z is directly bonded to an O or N atom, z is 0 and otherwise z is 1;

In one embodiment, the $R^7$ groups are the same. In particular, the $R^7$ groups may be $C_{1-4}$ alkyl, in one embodiment, methyl. In one embodiment, at least one $R^7$ group is $C_{1-4}$ alkyl.

In one embodiment, both $R^{7C}$ groups are the same. In particular, the $R^{7C}$ groups may be hydrogen.

In one embodiment, e is 1 or 2. In a further embodiment, e is 2.

Preferably, Z is a group of formula (IVB), in particular, a group of formula (IVB), wherein all $R^4$ groups are methyl groups and b is 2. In this embodiment, the zwitterionic group is a phosphorylcholine (PC) group.

n is an integer which defines the number of zwitterionic groups which are present in the polymerisable material of formula (I). n may be 1, 2 or 3. Preferably, n is 1 or 2.

is an integer which defines the number of zwitterionic groups which are present in the polymerisable material of formula (II). p may be 1, 2 or 3. Preferably, p is 1 or 2.

v is an integer which defines the number of $[(X)_m—Y^3(Z)_p]$ groups which are present in the polymerisable material of formula (II). p may be 1, 2 or 3. Preferably, p is 1 or 2.

Exemplary Polymerisable Material of Formula (I)

In one embodiment, the polymerisable material of the present invention has the formula (IA):

wherein "OPC" is a zwitterionic group of formula (IVB), wherein all $R^4$ groups are methyl and b is 2, w is an integer from 1 to 500, r' and r" may be the same or different and are each independently an integer from 0 to 10, preferably 4 to 6.

Accordingly, in one embodiment, the polymerisable material of the present invention is a material of formula (I), wherein X is a methacrylate group, $Y^1$ is $(CH_2CH_2O)_{r'}$ $(CH_2)_3$, W is a group of formula (IIIA), w is an integer from 1 to 500, $Y^2$ is $(CH_2)_3(CH_2CH_2O)_{r''}$, Z is a group of formula (IVB) wherein all $R^4$ groups are methyl and b is 2, m is 1, n is 1 and r' and r" may be the same or different and are each independently an integer between 0 and 10, preferably 4 to 6.

In one embodiment of the invention, the polymerisable material is a material of formula (IB):

wherein "OPC" is a zwitterionic group of formula (IVB), wherein all $R^4$ groups are methyl and b is 2 and w is 0 to 15.

Accordingly, in one embodiment, the polymerisable material of the present invention is a material of formula (I), wherein X is a methacrylate group, $Y^1$ is $(CH_2)_3$, w is 0 to 15, preferably 2 to 4, $Y^2$ is $(CH_2)_3$, Z is a group of formula (IVB) wherein all $R^4$ groups are methyl and b is 2, m is 1 and n is 2.

Exemplary Polymerisable Material of Formula (II)

In one embodiment of the present invention, the polymerisable monomer of the present invention has the formula (IIA):

(IIA)

wherein "OPC" is a zwitterionic group of formula (IVB), wherein all $R^4$ groups are methyl and b is 2.

Accordingly, in one embodiment, the polymerisable material of the present invention is a material of formula (II), wherein X is a methacrylate group, $Y^3$ is —$(CH_2)_3$—O—$(CH_2)_3$—, Z is a group of formula (IVB) wherein all $R^4$ groups are methyl and b is 2, W is a group of formula (IIIC), R' is methyl, p is 1 and v is 1.

In an alternative embodiment of the present invention, the polymerisable material of the present invention has the formula (IIB).

(IB)

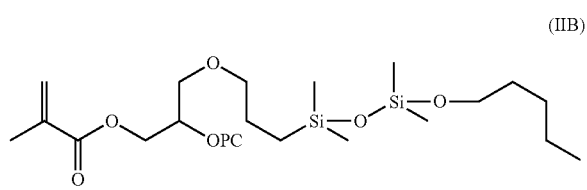

(IIB)

wherein "OPC" is a zwitterionic group of formula (IVB), wherein all $R^4$ groups are methyl and b is 2.

Accordingly, in one embodiment, the polymerisable material of the present invention is a material of formula (II), wherein X is a methacrylate group, $Y^3$ is —$(CH_2)_3$—O—$(CH_2)_3$—, Z is a group of formula (IVB), wherein all $R^4$ groups are methyl and b is 2, W is a group of formula (IIIA), $R^1$ is $(CH_2)_4CH_3$, p is 1 and v is 1.

In one embodiment the polymerisable material of the present invention has the formula (IIC):

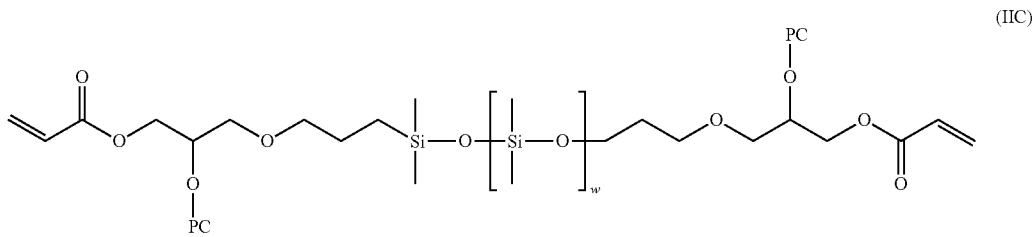

wherein "OPC" is a zwitterionic group of formula (IVB), wherein all $R^4$ groups are methyl and b is 2 and w is an integer from 1 to 500.

Accordingly, in one embodiment, the polymerisable material of the present invention is a material of formula (II), wherein X is an acrylate group, $Y^3$ is —$(CH_2)$—$(CH(OZ))$—$CH_2$—O—$(CH_2)_3$—, Z is a group of formula (IVB), wherein all $R^4$ groups are methyl and b is 2, W is a group of formula (IIIA), $R^1$ is methyl, p is 1 and v is 2.

The polymerisable materials of the present invention may be polymerised to produce a polymer which is clear and which is useful in the production of ophthalmic devices such as contact lenses. The term "clear" is used herein to refer to polymers (and articles formed therefrom) which appear transparent and non-opaque to the visible eye. In one embodiment, these materials have an optical transmission of about 80% or more, about 85% or more, about 90% or more, about 95% or more, about 99% or more.

Thus, in a second aspect, the invention provides a method of producing a polymer comprising polymerising a polymerisable material as defined herein.

In one embodiment, further components may be mixed with the polymerisable material, prior to polymerisation, to form a polymerisable system. Examples of further components include hydrophilic monomers, macromere, UV absorbers, tinting agents, antibacterial agents, therapeutic agents, pigments, non-reactive diluents, cross-linking agents, initiating species and combinations thereof.

The term "hydrophilic" as used to describe the monomers which may form a part of the polymerisable system is intended to have its normal meaning, specifically it is used to describe monomers which have an affinity for water. Hydrophilic monomers are monomers which contain a group capable of being involved in a polymerisation reaction and at least one hydrophilic group. Examples of hydrophilic groups are polar groups such as hydroxyl, amide, acid, lactam and the like. In one embodiment, the hydrophilic monomer is selected from the group consisting of N-vinyl pyrrolidone, methacrylic acid, glycerol monomethacrylate, dimethylacrylamide, hydroxypropyl (meth)acrylate and isomers, and 2-hydroxyethyl(meth)acrylate (HEA and HEMA). Where present, hydrophilic monomers may be included in an amount in the range from about 0.1 to about 75 wt %, in one embodiment, about 1 to about 70 wt %, in one embodiment, about 5 to about 60 wt %, in one embodiment, about 10 to about 15 wt % based on the weight of the polymerisable system.

Where present, a non-reactive diluent is generally included in the polymerisable system in small amounts, typically of the order of about 1 to about 25 wt %, preferably about 2 to about 10 wt % based on the weight of the polymerisable system. The skilled person will be familiar with suitable non-reactive diluents. In principle, suitable diluents are all solvents which dissolve the other monomers present in the polymerisable solution, for example, water, alcohols, e.g. methanol, ethanol and glycol, carboxylic acid amides such as dimethylformamide, dipolar aprotic solvents, such as dimethyl sulfoxide or methyl ethyl ketone, ketones, such as acetone or cyclohexanone, hydrocarbons such as toluene, ethers such as THF, dimethoxyethane or dioxane and halogenated hydrocarbons such as trichloroethane and combinations thereof.

Alternatively or in addition, a cross-linking agent may be added to the polymerisation system. Any cross-linking agent may be used and the skilled person will be familiar with suitable cross-linking agents. Examples of suitable cross-linking agents include ethylene glycol dimethacrylate (EGDMA), trimethylolpropane trimethacrylate (TMPTMA), glycerol trimethacrylate, polyethyleneglycol dimethacrylate and other polyacrylate and polymethacrylate esters. Further examples of suitable cross-linking agents are the macromeric cross-linking agents described in U.S. Pat. No. 5, 849,811, siloxane cross-linking agents and oxybis(ethyleneoxyethylene) bis(2-methylprop-2-enoate) ($CH_2$=$CH(Me)CO_2$ ($CH_2CH_2OCH_2CH_2OCH_2CH_2OCH_2CH_2)_2$). In one embodiment, the polymerisable material of the present invention includes a functionality which acts as a cross-linking agent and hence in such an embodiment, it is not necessary to add a separate cross-linking agent to the system even where it is desirable to produce a cross-linked polymer.

The cross-linking agent may be included in an amount in the range from about 0.1 to about 10 wt %, in one embodiment, about 0.2 to about 8 wt %, in one embodiment, about 0.5 to about 7 wt %, in one embodiment, about 1 to about 6 wt % based on the weight of the polymerisable system.

Alternatively or in addition, an initiating species may be added to the polymerisation system. The skilled person will be familiar with suitable initiating species and examples include benzoyl peroxide, 2,2'-azo-bis(2-methylpropionitrile) or benzoin methyl ether.

In one embodiment, the polymerisable material of the present invention may be used to produce a bulk cross-linked polymer. This is advantageous where the polymerisable material is to be used to provide polymers which are useful in the ophthalmic field.

In an alternative embodiment, the polymerisable material of the present invention may be used to produce a solution polymer. This is advantageous where the polymer is to be used to bicompatabilise a surface.

For both bulk and solution polymerisations, the polymerisation step may be a conventional polymerization reaction, for example by thermal or photochemical polymerization. For thermal polymerisation, a temperature in the range from 40 to 100° C., typically 50 to 80° C. may be used. For a photochemical polymerisation, actinic radiation such as gamma, UV, visible or microwave radiation may be use. Typically UV radiation of wavelength 200 to 400 nm is used.

In one embodiment, polymerisation may be performed in the presence of a solvent with which the groups present in the polymerisable material will not react under the polymerisation conditions used, for example water, alcohols, such as ethanol, methanol and glycol, and furthermore carboxylic acid amides, such as dimethylformamide, dipolar aprotic solvents, such as dimethyl sulfoxide or methyl ethyl ketone, ketones for example acetone or cyclohexanone, hydrocarbons, for example toluene, ethers, for example THF, dimethoxyethane or dioxane and halogenated hydrocarbons, for example trichloroethane and also mixtures of suitable solvents, for example mixtures of water with an alcohol, for example a water/ethanol or water/methanol mix. Any mixtures of these solvents may be used.

For example, where the polymerisable material is used to form a bulk polymer which will be used in ophthalmic applications, the addition of a small amount (e.g. 2 to 10 wt %) of a non-reactive solvent may aid with mold release where polymerisation is performed directly in a mold, may aid with extraction of unwanted components and/or reduce changes in lens dimensions when the molded lenses are hydrated.

As described above, the polymerisation may be carried out in the presence of one or more polymerisation initiators, such as benzoyl peroxide, 2,2'-azo-bis(2-methylpropionitrile) or benzoin methyl ether. Other polymerisation initiators which may be used are dislosed in "Polymer Handbook", 3rd Edition, Ed. J. Brandrup and E. H. Immergut, Pub. Wiley-Interscience, New York 1989.

Where a solution polymerisation is carried out to produce a soluble polymer, the polymer is generally purified by dialysis, precipitation in a non-solvent (e.g. diethyl ether or acetone) or ultrafiltration. The resulting polymer is generally dried under vacuum e.g. for 5 to 72 hours and has a molecular weight from 3,000 to 10 million, in one instance, from 20,000 to 1 million, in an alternative instance, from 50,000 to 750,000, in an alternative instance, from 50,000 to 500,000.

Furthermore, where the aim is to provide a biocompatible coating and co-monomers capable of producing post polymerisation cross-linking are present in the monomer mixture, the polymerisation conditions are set such that cross-linking does not occur during polymerisation. For example, actinic radiation would not be used to prepare polymers containing a co-monomer which can form crosslinks by exposure to actinic radiation.

Generally, the duration of the polymerisation step will depend on the technique which is used to form the end article. For example, where the polymer produced is a bulk polymer and it is to be used to form an ophthalmic lens, the lens may be formed by cast molding or by forming a larger bulk material which is then cut down into lenses. In the former case, the polymerisation time may be in the range from 1 second to 1 hour. In the latter case, polymerisation times may range from 0.1 to 72 hours, in one embodiment, 0.1 to 1 hours, in an alternative embodiment, 8 to 48 hours, for instance 16 to 24 hours and under an inert atmosphere of, for example, nitrogen or argon.

The bulk polymers which can be obtained by the method of the present invention i.e. by polymerising a polymerisable material as defined herein, are particularly useful in ophthalmic applications. In this regard, the present invention further provides a polymer obtainable by the methods described herein.

In one embodiment, the present invention provides a xerogel comprising a polymer obtained by the method of the present invention and which is essentially free from water.

After a polymer (or xerogel) has been synthesized, the method of the present invention may comprise a further step of hydrating the polymer to form a silicone hydrogel. The polymer formed may be hydrated by standard techniques with which the person skilled in the art will be familiar. For example, the polymer may be hydrated by soaking in phosphate-buffered saline. Thus, the present invention further provides a silicone hydrogel comprising a polymer obtained by the method of the present invention and water in an amount of 10 to 80% by weight of the hydrogel.

The polymers of the present invention have a balance of properties, such as clarity, gas permeability and water content which makes them particularly useful.

In one embodiment, the polymer of the present invention has an equilibrium water content of 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 95% or more. In one embodiment, the water content of the polymer is in the range from about 20 to about 60%, preferably about 30 to about 50%.

Alternatively or in addition, the polymers of the present invention may have a tensile modulus (modulus of elasticity, E) of less than about 3 MPa. In one embodiment, the tensile modulus is in the range from 0.2 to about 2.5 MPa, in one instance about 0.3 to 1.5 MPa, preferably about 0.4 to about 1 MPa.

Alternatively or in addition, the polymers of the present invention may have an optical transmission of about 80% or more, about 85% or more, about 90% or more, about 95% or more, about 99% or more. In a preferred embodiment, the polymers of the present invention are transparent and/or clear which is particularly advantageous where they are used to form an ocular device.

The properties of the polymers of the present invention mean that they are particularly suitable for use in ophthalmic applications. Therefore, in a further aspect, the present invention provides an article, in particular an ocular device, comprising a polymer as defined herein. Preferably, the ocular device is an ophthalmic lens, preferably a contact lens.

An ophthalmic lens is a lens which, in use, will be placed in intimate contact with the eye or tear fluid. The term "ophthalmic lens" is intended to include contacts lenses for vision correction, contact lenses for changing eye colour, ophthalmic drug delivery devices and ocular tissue protective devices.

The ophthalmic lenses of the present invention may be manufactured by transferring the polymerisable solution into a lens mold cavity and initiating polymerization. Initiators, including photoinitiators, which are commercially available may be added to the mixture to aid initiation of the polymerization. As described previously, polymerization may be initiated by a number of well known techniques depending on the exact nature of the mixture. Examples of suitable techniques include application of radiation such as microwave, e-beam or ultraviolet. Alternatively, polymerization may be initiated thermally. Where the ophthalmic lenses are manufactured in this way, it may be advantageous to include a diluent in the homogeneous polymerisable solution as it aids with extraction from the mold. It also helps to ensure that the molded polymer retains the same shape and dimensions when it is hydrated to form a silicone hydrogel.

Alternatively, the ophthalmic lenses of the present invention may be prepared by polymerising the homogeneous polymerisable mixture to form a product which can then be formed into the appropriate shape by cutting and lathing.

In contrast to other tissues which receive oxygen from blood flow, the cornea receives oxygen primarily from the corneal surface which is exposed to the environment.

Therefore, an ophthalmic lens which is intended to be worn on the eye for extended periods of time must allow sufficient oxygen to permeate through the lens in order to sustain corneal health. It is possible to detect when the cornea has received an inadequate supply of oxygen because it will swell. Preferably, the oxygen permeability of the ophthalmic lenses of the present invention is sufficient to prevent any clinically significant swelling of the cornea from occurring. In one embodiment, the extent of corneal swelling observed is about 10% or less over at least 8 hours, about 8% or less over at least 8 hours, about 6% or less over at least 8 hours, about 4% or less over at least 8 hours, about 2% or less over at least 8 hours, about 1% or less over at least 8 hours.

In this regard, preferably an ophthalmic lens of the present invention is suitable for extended wear. Advantageously, the ophthalmic lenses of the present invention may be worn by a user for up to 4 days or more, in one embodiment 7 days or more, in one embodiment 14 days or more, in one embodiment 30 days or more, without causing substantial corneal damage or user discomfort.

Accordingly, in one embodiment, the article of the present invention has an oxygen permeability of about 30 barriers or more, preferably about 40 barriers or more, preferably about 50 barriers or more, preferably about 60 barriers or more.

Alternatively or in addition, the article of the present invention has an equilibrium water content of 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 95% or more. In one embodiment, the water content of the polymer is in the range from about 20 to about 60%, preferably about 30 to about 50%.

Alternatively or in addition, the articles of the present invention may have a tensile modulus (modulus of elasticity, E) of less than about 3 MPa. In one embodiment, the tensile modulus is in the range from 0.2 to about 2.5 MPa, in one instance about 0.3 to 1.5 MPa, preferably about 0.4 to about 1 MPa.

Alternatively or in addition, the articles of the present invention may have an optical transmission of about 80% or more, about 85% or more, about 90% or more, about 95% or more, about 99% or more. In a preferred embodiment, the articles of the present invention are transparent and/or clear which is particularly advantageous where the article is an ocular device.

Alternatively or in addition, the articles of the present invention may have a % of scattered visible light (haze) of <100%, in one embodiment, <80%, in one embodiment, <60%, in one embodiment <50%, measured according to the standard ASTM D 1003.

Alternatively, as described above, the polymerisable material of the present invention may be used to form polymers which can be used to biocompatibilise a surface. Thus, in a further aspect, the present invention provides a process for biocompatibilising a surface comprising coating the surface with a polymer of the present invention. The invention further provides an article comprising a surface having coated thereon a polymer as defined herein. The polymers of the present invention may be used to coat many different surfaces, depending on the nature of the groups which are present in the polymer and capable of binding it to the surface.

Coating of a surface with the polymer may generally be carried out by coating the surface with a solution or dispersion of the polymer, generally in an alcoholic, aqueous, organic or halogenated solvent or a mixture thereof. Examples of suitable solvents include methanol, ethanol, dichloromethane and freon. Coating may be carried out at room temperature or at an elevated temperature. Generally, coating is carried out at a temperature in the range from 5 to 60° C.

Surfaces may be coated with the polymers of the present invention by known techniques, such as dip-coating, spray-coating, web-coating or spin coating.

In one embodiment, the polymer is coated onto the surface in the form of a microdispersion, such as a microemulsion.

After coating, where the polymer of the present invention includes cross-linkable groups, it may be subjected to a cross-linking reaction. The cross-linking may be carried out by known methods, for example thermally, using actinic radiation, using reactive gases, for example ammonia, by changing the pH, using difunctional additives or by using activation chemistries, for example by known methods as described in "Methods in Enzymology, volume 135, Immobilised Enzymes and Cells, part B", Ed. K. Mosbach, Academic Press Inc., New York, 1987. In cases where crosslinking is achieved thermally or by gas treatment, the treatment may be carried out on the dried coating. Alternatively, where the pH needs to be changed or additives need to be included, treatment may be performed on the coated material in a solution which does not remove the coating. In some embodiments, crosslinking may be carried out with the coating hydrated which facilitates the crosslinking reaction.

The polymers of the present invention may be used to coat a surface of materials which can be used as a construction material for implants or prostheses for the human or animal body, particularly where these implants or prostheses have direct physical contact with blood and where biocompatibility and haemocompatibility are required. They can also be used in the construction of membranes and other devices that are to be brought into contact with blood or other body fluids on an extra-corporeal basis, for example in heart-lung machines or artificial kidneys.

The polymers of the present invention may also be used to coat materials used in processing applications, for example separation membranes and process equipment and tubing. In particular, the polymers of the present invention may be used to modify the surface properties of biofiltration membranes in bioreactors and fermentation systems where the membranes come into direct contact with complex biological solutions containing e.g. proteins, polysaccharides, fats and whole cells. The polymers of the present invention may be useful in reducing membrane fouling by components of a process solution.

When the polymers of the present invention are used to coat the surface of a material which is then used in the construction of finished devices, it may be necessary to take precautionary steps to ensure that the coated surface is not damaged and the effectiveness of the treatment reduced before the finished device is produced.

The polymers of the present invention may be used to coat finished implants, prostheses, membranes, catheters, contact lenses, intraocular lenses, and other devices to impart biocompatibility to the article.

Therefore, in a further aspect, the present invention provides an article comprising a surface having a coating thereon of a polymer of the present invention.

In one embodiment, the article is an ocular device, in particular an ophthalmic lens, in particular a contact lens.

Several illustrative embodiments of the invention are described by the following enumerated clauses:

1. A polymerisable material of formula (I) or (II):

$$(X-Y^1)_m-W(Y^2-Z)_n \quad (I)$$

$$[(X)_m-Y^3(Z)_p]_v-W-R^1 \quad (II)$$

wherein
X is a polymerisable group;
$Y^1$ and $Y^2$ are each independently a linker group selected from the group consisting of a bond, $C_{1-12}$ alkylene, $C_{2-12}$ alkenylene, $C_{2-12}$ alkynylene, $C_{3-12}$ cycloalkylene, $C_{3-12}$ cycloalkenylene, $C_{2-12}$ heteroalkenylene, $C_{2-12}$ heteroalkynylene, arylene, heteroarylene, —C(O)—$C_{1-12}$ alkylene, —C(S)—$C_{1-12}$ alkylene, —C(O)O—$C_{1-12}$ alkylene, —C(O)S—$C_{1-12}$ alkylene, —C(O)N($R^M$)—$C_{1-12}$ alkylene, —C(S)—$C_{1-12}$ alkylene, —C(S)O—$C_{1-12}$ alkylene, —C(S)S—$C_{1-12}$ alkylene, —C(S)N($R^M$)—$C_{1-12}$ alkylene, —(CH$_2$)$_q$(OCH$_2$CH$_2$)$_r$— and —(CH$_2$CH$_2$O)$_r$(CH$_2$)$_q$—, wherein $R^M$ is hydrogen or $C_{1-4}$ alkyl, q is an integer from 1 to 10, r is an integer from 1 to 10, wherein one or more carbon atoms in the $C_{1-12}$ alkylene group may be optionally replaced with a heteroatom selected from the group consisting of S and O and the alkylene, alkenylene, alkynylene, cycloalkylene, cycloalkenylene, heteroalkenylene, heteroalkynylene, arylene and heteroarylene groups may be optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O;
$Y^3$ is a linker group;
$R^1$ is a $C_{1-12}$ alkyl group, optionally substituted with one or more $R^N$;
W is a siloxane group-containing component;
Z is a zwitterionic group;
m is an integer from 1 to 10;
n is an integer from 1 to 3;
p is an integer from 1 to 3; and
v is an integer from 1 to 3.

2. A polymerisable material according to clause 1, wherein X is a polymerisable group selected from the group consisting of acrylates, methacrylates, styrenes, vinyls and multi-functionalised derivatives.

3. A polymerisable material according to clause 2, wherein X is a methacrylate group.

4. A polymerisable material according to any one of clauses 1 to 3, wherein $Y^3$ is selected from the group consisting of a bond, $C_{1-12}$ alkylene, $C_{2-12}$ alkenylene, $C_{2-12}$ alkynylene, $C_{3-12}$ cycloalkylene, $C_{3-12}$ cycloalkenylene, $C_{1-12}$ heteroalkylene $C_{2-12}$ heteroalkenylene, $C_{2-12}$ heteroalkynylene, arylene, heteroarylene, —C(O)—$C_{1-12}$ alkylene, —C(S)—$C_{1-12}$ alkylene, —C(O)O—$C_{1-12}$ alkylene, —C(O)S—$C_{1-12}$ alkylene, —C(O)N($R^M$)—$C_{1-12}$ alkylene, —C(S)—$C_{1-12}$ alkylene, —C(S)O—$C_{1-12}$ alkylene, —C(S)S—$C_{1-12}$ alkylene, —C(S)N($R^M$)—$C_{1-12}$ alkylene, wherein $R^M$ is hydrogen or $C_{1-4}$ alkyl, wherein the alkylene, alkenylene, alkynylene, cycloalkylene, cycloalkenylene, heteroalkenylene, heteroalkynylene, arylene and heteroarylene groups may be optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O.

5. A polymerisable material according to any preceding clause, wherein the monomer is of formula (I) and wherein $Y^1$ and $Y^2$ are both $C_{1-12}$ alkylene, wherein one or more carbon atoms of the alkylene group have been replaced with a heteroatom selected from the group consisting of O and S.

6. A polymerisable material according to clause 5, wherein $Y^1$ is —(CH$_2$CH$_2$O)$_r$—(CH$_2$)$_3$— and $Y^2$ is —(CH$_2$)$_3$(CH$_2$CH$_2$O)$_r$—, wherein r is an integer in the range from 1 to 10.

7. A polymerisable material according to clause 4, wherein the monomer is of formula (II) and wherein $Y^3$ is $C_{1-12}$ heteroalkylene.

8. A polymerisable material according to clause 7, wherein the monomer is of formula (II) and wherein $Y^3$ is —(CH$_2$)$_3$—O—(CH$_2$)$_3$—.

9. A polymerisable material according to any preceding clause, wherein W is a siloxane group of formula (IIIA):

(IIIA)

wherein each R is independently selected from hydrogen or a $C_{1-12}$ alkylene, $C_{2-12}$ alkenylene, $C_{2-12}$ alkynylene, $C_{3-12}$ cycloalkylene, $C_{3-12}$ cycloalkenylene, $C_{1-12}$ heteroalkylene, $C_{2-12}$ heteroalkenylene, $C_{2-12}$ heteroalkynylene, arylene, heteroarylene group, optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O and w is an integer from 1 to 500.

10. A polymerisable material according to any preceding clause, wherein W is a siloxane group of formula (IIIB):

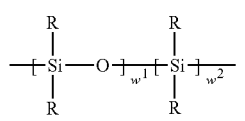

(IIIB)

wherein each R is independently selected from hydrogen or a $C_{1-12}$ alkylene, $C_{2-12}$ alkenylene, $C_{2-12}$ alkynylene, $C_{3-12}$ cycloalkylene, $C_{3-12}$ cycloalkenylene, $C_{1-12}$ heteroalkylene, $C_{2-12}$ heteroalkenylene, $C_{2-12}$ heteroalkynylene, arylene, heteroarylene group, optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O and $w^1$ and $w^2$ are each independently an integer in the range from 1 to 500

11. A polymerisable material according to any one of clauses 1 to 3, wherein W is a siloxane group of formula (IIIC):

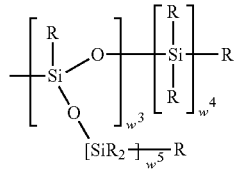

wherein each R is independently selected from hydrogen or a $C_{1-12}$ alkylene, $C_{2-12}$ alkenylene, $C_{2-12}$ alkynylene, $C_{3-12}$ cycloalkylene, $C_{3-12}$ cycloalkenylene, $C_{1-12}$ heteroalkylene, $C_{2-12}$ heteroalkenylene, $C_{2-12}$ heteroalkynylene, arylene, heteroarylene group, optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O and $w^3$, $w^4$ and $w^5$ are each independently an integer in the range from 1 to 500.

12. A polymerisable material according to any one of clauses 1 to 3, wherein W is a siloxane group of formula (IIID):

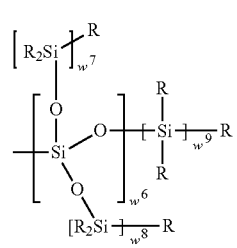

(IIID)

wherein each R is independently selected from hydrogen or a $C_{1-12}$ alkylene, $C_{2-12}$ alkenylene, $C_{2-12}$ alkynylene, $C_{3-12}$ cycloalkylene, $C_{3-12}$ cycloalkenylene, $C_{1-12}$ heteroalkylene, $C_{2-12}$ heteroalkenylene, $C_{2-12}$ heteroalkynylene, arylene, heteroarylene group, optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O and $w^6$, $w^7$, $w^8$ and $w^9$ are each independently an integer in the range from 1 to 500.

13. A polymerisable material according to any preceding clause, wherein Z is a group wherein Z is a zwitterionic group selected from the group consisting of (IVA), (IVB), (IVC), (IVD) and (IVE), wherein group (IVA) has the formula:

(IVA)

wherein each $R^3$ and $R^{3A}$ is independently selected from hydrogen and $C_{1-4}$ alkyl and a is an integer from 2 to 4; group (IVB) has the formula:

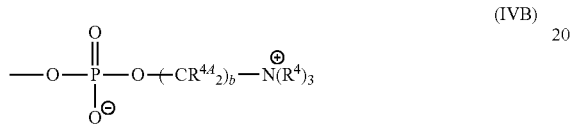

(IVB)

wherein each $R^4$ and $R^{4A}$ is independently selected from hydrogen and $C_{1-4}$ alkyl and b is an integer from 1 to 4; group (IVC) has the formula:

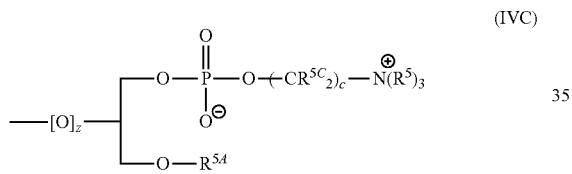

(IVC)

wherein each $R^5$ and $R^{5C}$ is independently selected from hydrogen and $C_{1-4}$ alkyl; $R^{5A}$ is hydrogen or a group —C(O)B$^1$R$^{5B}$, wherein R$^{5B}$ is hydrogen or methyl, B$^1$ is selected from the group consisting of a bond; $C_{1-10}$ alkylene, $C_{2-10}$ alkenylene, $C_{2-10}$ alkynylene, $C_{3-10}$ cycloalkylene, $C_{3-10}$ cycloalkenylene, $C_{1-10}$ heteroalkylene, $C_{2-10}$ heteroalkenylene, $C_{2-10}$ heteroalkynylene, arylene, heteroarylene, —C(O)R$^M$—, —C(O)OR$^M$—, wherein R$^M$ is selected from the group consisting of $C_{1-10}$ alkylene, $C_{2-10}$ alkenylene and $C_{2-10}$ alkynylene, and wherein the alkylene, alkenylene, alkynylene, cycloalkylene, cycloalkenylene, heteroalkylene, heteroalkenylene, heteroalkynylene, arylene and heteroarylene groups may be optionally substituted with one or more R$^N$, wherein each R$^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —(C$_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O, and c is an integer from 1 to 4, wherein if Z is directly bonded to an O or N atom, z is 0 and otherwise z is 1;

group (IVD) has the formula:

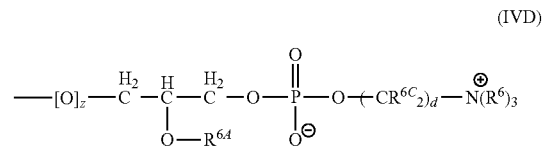

(IVD)

wherein each $R^6$ and $R^{6C}$ is independently selected from hydrogen and $C_{1-4}$ alkyl; $R^{6A}$ is hydrogen or a group —C(O)B$^2$R$^{6B}$, wherein R$^{6B}$ is hydrogen or methyl, B$^2$ is selected from the group consisting of a bond; $C_{1-10}$ alkylene, $C_{2-10}$ alkenylene, $C_{2-10}$ alkynylene, $C_{3-10}$ cycloalkylene, $C_{3-10}$ cycloalkenylene, $C_{1-10}$ heteroalkylene, $C_{2-10}$ heteroalkenylene, $C_{2-10}$ heteroalkynylene, arylene, heteroarylene, —C(O)R$^M$—, —C(O)OR$^M$—, wherein R$^M$ is selected from the group consisting of $C_{1-10}$ alkylene, $C_{2-10}$ alkenylene and $C_{2-10}$ alkynylene, and wherein the alkylene, alkenylene, alkynylene, cycloalkylene, cycloalkenylene, heteroalkylene, heteroalkenylene, heteroalkynylene, arylene and heteroarylene groups may be optionally substituted with one or more R$^N$, wherein each R$^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —(C$_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O, and d is an integer from 1 to 4, wherein if Z is directly bonded to an O or N atom, z is 0 and otherwise z is 1;

group (IVE) has the formula:

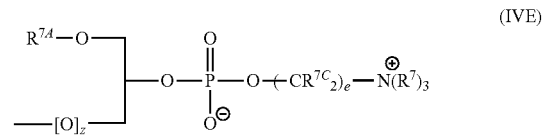

(IVE)

wherein each $R^7$ and $R^{7C}$ is independently selected from hydrogen and $C_{1-4}$ alkyl; $R^{7A}$ is hydrogen or a group —C(O)$B^2R^{7B}$, wherein $R^{7B}$ is hydrogen or methyl, $B^2$ is selected from the group consisting of a bond; $C_{1-10}$ alkylene, $C_{2-10}$ alkenylene, $C_{2-10}$ alkynylene, $C_{3-10}$ cycloalkylene, $C_{3-10}$ cycloalkenylene, $C_{1-10}$ heteroalkylene, $C_{2-10}$ heteroalkenylene, $C_{2-10}$ heteroalkynylene, arylene, heteroarylene, —C(O)$R^M$—, —C(O)O$R^M$—, wherein $R^M$ is selected from the group consisting of $C_{1-10}$ alkylene, $C_{2-10}$ alkenylene and $C_{2-10}$ alkynylene, and wherein the alkylene, alkenylene, alkynylene, cycloalkylene, cycloalkenylene, heteroalkylene, heteroalkenylene, heteroalkynylene, arylene and heteroarylene groups may be optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —(C$_0$-C$_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O, and e is an integer from 1 to 4, wherein if Z is directly bonded to an O or N atom, z is 0 and otherwise z is 1.

14. A polymerisable material according to clause 13, wherein Z is a zwitterionic group of formula (IVB).

15. A polymerisable material according to clause 14, wherein $R^4$ is methyl and b is 2.

16. A polymerisable material of formula (II) according to clause 1, having the structure:

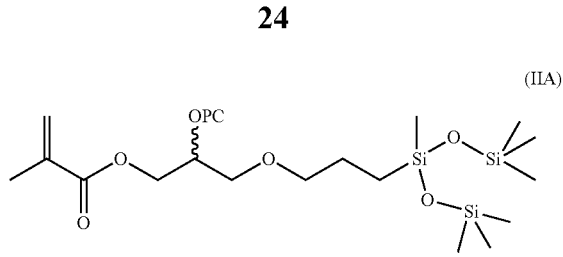

(IIA)

wherein "OPC" is a zwitterionic group of formula (IVB), wherein all $R^4$ groups are methyl and b is 2.

17. A polymerisable material of formula (II) according to clause 1, having the structure:

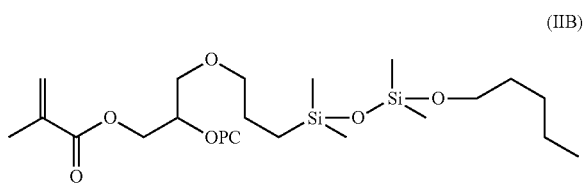

(IIB)

wherein "OPC" is a zwitterionic group of formula (IVB), wherein all $R^4$ groups are methyl and b is 2.

18. A polymerisable material of formula (II) according to clause 1, having the structure:

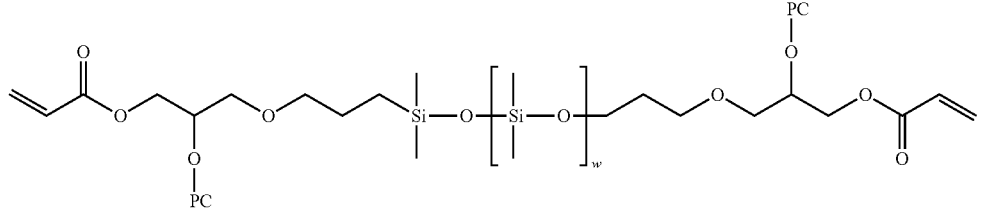

(IIC)

wherein "OPC" is a zwitterionic group of formula (IVB), wherein all $R^4$ groups are methyl and b is 2, w is an integer from 1 to 500

19. A polymerisable material of formula (I) according to clause 1, having the structure:

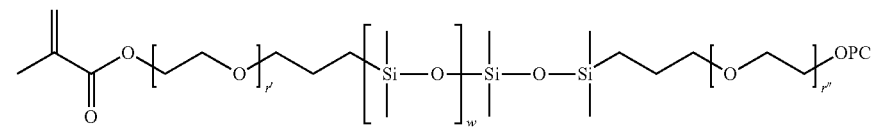

(IA)

wherein "OPC" is a zwitterionic group of formula (IVB), wherein all $R^4$ groups are methyl and b is 2, w is an integer from 1 to 500, r' and r" are the same or different and are each independently an integer between 0 and 10.

20. A polymerisable material of formula (I) according to clause 1, having the structure:

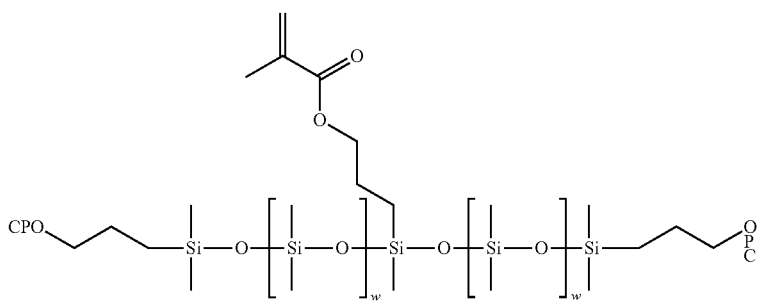

wherein "OPC" is a zwitterionic group of formula (IVB), wherein all $R^4$ groups are methyl and b is 2 and w is from 0 to 15.

21. A method for producing a polymer comprising polymerising a polymerisable material as defined in any preceding clause.
22. A polymer obtainable by polymerising a polymerisable material as defined in any one of clauses 1 to 20.
23. A xerogel comprising a polymer as defined in clause 22, which is free from water.
24. A silicone hydrogel comprising a polymer as defined in clause 22, and water in an amount of 30 to 80% by weight of hydrogel.
25. A polymer according to clause 22, which has an equilibrium water content in the range from 30 to 50%.
26. A polymer according to clause 22 or clause 25, which has a modulus in the range from 0.5 to 1.0 MPa.
27. An article comprising a polymer as defined in any one of clauses 22 to 26.
28. An article according to clause 27, which is a contact lens.
29. A contact lens according to clause 28, which has an oxygen permeability of about 30 barriers or more.
30. A contact lens according to clause 28 or clause 29, which has an equilibrium water content in the range from 30 to 50%.
31. An article comprising a surface having coated thereon a polymer as defined in any one of clauses 22 to 26.
32. An article according to clause 31, which is a contact lens.
33. A method of coating an article having a surface comprising applying a polymer as defined in any one of clauses 22 to 26 to the surface of the article.

Chemical Groups
Halo

The term "halogen" (or "halo") is used herein to refer to fluorine, chlorine, bromine and iodine.

Carbonyl and Carboxy

The term "carbonyl" is used herein to refer to a carbon connected with a double bond to an oxygen atom, and tautomeric forms thereof. A carbonyl group may also be denoted as —C(O)—. Examples of moieties that contain a carbonyl include but are not limited to aldehydes —C(O)H, ketones —C(O)—($C_1$-$C_{10}$ alkyl)-, carboxylic acids —$CO_2$H and amides —C(O)$NH_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl) and esters -C(O)—O($C_1$-$C_{10}$ alkyl).

Thiocarbonyl and Thiocarboxy

The terms "thiocarbonyl" and "thiocarboxy" are used herein to refer to a carbon connected via a double bond to a sulfur atom, and tautomeric forms thereof.

Alkyl, Alkenyl, Cycloalkyl Etc.

The term "alkyl" is used herein to refer to monovalent straight chain or branched, saturated, acyclic hydrocarbyl groups. In one embodiment, alkyl is $C_{1-10}$alkyl, in another embodiment $C_{1-6}$alkyl, in another embodiment $C_{1-4}$alkyl, such as methyl, ethyl, n-propyl, i-propyl or i-, n-, secondary or t-butyl groups.

The term "cycloalkyl" is used herein to refer to monovalent, saturated, cyclic hydrocarbyl groups. In one embodiment, cycloalkyl is $C_{3-10}$cycloalkyl, in another embodiment, $C_{3-6}$cycloalkyl, such as cyclopentyl and cyclohexyl.

The term "alkenyl" is used herein to refer to monovalent straight or branched, unsaturated, acyclic hydrocarbyl groups having at least one carbon-carbon double bond and, in one embodiment, no carbon-carbon triple bonds. In one embodiment alkenyl is $C_{2-10}$alkenyl, in another embodiment, $C_{2-6}$alkenyl, in another embodiment $C_{2-4}$alkenyl.

The term "cycloalkenyl" is used herein to refer to monovalent, unsaturated, cyclic hydrocarbyl groups. In one embodiment, cycloalkenyl is $C_{3-10}$cycloalkyl, in another embodiment, $C_{3-6}$cycloalkyl, such as cyclopentenyl and cyclohexenyl.

The term "alkynyl" is used herein to refer to monovalent straight or branched, unsaturated, acyclic hydrocarbyl groups having at least one carbon-carbon triple bond. In one embodiment alkynyl is $C_{2-10}$alkynyl, in another embodiment, $C_{2-6}$alkynyl, in another embodiment $C_{2-4}$alkynyl.

Heteroalkyl, heterocyclyl etc.

The term "heteroalkyl" is used herein to refer to monovalent alkyl groups in which up to three carbon atoms, in one embodiment up to two carbon atoms, in another embodiment one carbon atom, are each replaced independently by O, $S(O)_q$ or N, provided at least one of the alkyl carbon atoms remains. The heteroalkyl group may be C-linked or hetero-linked, i.e. it may be linked to the remainder of the molecule through a carbon atom or through O, $S(O)_q$ or N, wherein q is independently 0, 1 or 2.

The term "heterocyclyl" or "heterocyclic ring" is used herein to refer to monovalent, cycloalkyl groups or divalent cycloalkylene groups in which up to three carbon atoms, in one embodiment up to two carbon atoms, in another embodiment one carbon atom, are each replaced independently by O, $S(O)_q$ or N, provided at least one of the cycloalkyl carbon atoms remains.

Examples of heterocyclyl groups include oxiranyl, thiaranyl, aziridinyl, oxetanyl, thiatanyl, azetidinyl, tetrahydrofuranyl, tetrahydrothiophenyl, pyrrolidinyl, pyrazolidinyl, imidazolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thieazepanyl and 1,4-diazepanyl. Other examples include cyclic imides, cyclic anhydrides and thiazolidindiones. The heterocyclyl group may be C-linked or N-linked, i.e. it may be linked to the remainder of the molecule through a carbon atom or through a nitrogen atom.

Aryl etc.

The term "aryl" is used herein to refer to monovalent, aromatic, cyclic hydrocarbyl groups, such as phenyl or naphthyl (e.g. 1-naphthyl or 2-naphthyl). In general, the aryl group may be a monocyclic or polycyclic fused ring aromatic group. Preferred aryl groups are $C_6$-$C_{14}$aryl.

Other examples of aryl groups are monovalent radicals derived from aceanthrylene, acenaphthylene, acephenanthrylene, anthracene, azulene, chrysene, coronene, fluoranthene, fluorene, as-indacene, s-indacene, indene, naphthalene, ovalene, perylene, phenalene, phenanthrene, picene, pleiadene, pyrene, pyranthrene and rubicene.

Heteroaryl etc.

The term "heteroaryl" is used herein to refer to monovalent, heteroaromatic, cyclic hydrocarbyl groups additionally containing one or more heteroatoms independently selected from O, S, N and $NR^N$, wherein $R^N$ is preferably H, alkyl (e.g. $C_{1-6}$alkyl) or cycloalkyl (e.g. $C_{3-6}$cycloalkyl).

In general, the heteroaryl group may be a monocyclic or polycyclic (e.g. bicyclic) fused ring heteroaromatic group. In one embodiment, heteroaryl groups contain 5-13 ring members (preferably 5-10 members) and 1, 2, 3 or 4 ring heteroatoms independently selected from O, S, N and $NR^N$. In one embodiment, a heteroaryl group may be 5, 6, 9 or 10 membered, e.g. 5-membered monocyclic, 6-membered monocyclic, 9-membered fused-ring bicyclic or 10-membered fused-ring bicyclic.

Monocyclic heteroaromatic groups include heteroaromatic groups containing 5-6 ring members and 1, 2, 3 or 4 heteroatoms selected from O, S, N or $NR^N$.

In one embodiment, 5-membered monocyclic heteroaryl groups contain 1 ring member which is an —$NR^N$-group, an —O— atom or an —S— atom and, optionally, 1-3 ring members (e.g. 1 or 2 ring members) which are =N— atoms (where the remainder of the 5 ring members are carbon atoms).

Examples of 5-membered monocyclic heteroaryl groups are pyrrolyl, furanyl, thiophenyl, pyrazolyl, imidazolyl, isoxazolyl, oxazolyl, isothiazolyl, thiazolyl, 1,2,3 triazolyl, 1,2,4 triazolyl, 1,2,3 oxadiazolyl, 1,2,4 oxadiazolyl, 1,2,5 oxadiazolyl, 1,3,4 oxadiazolyl, 1,3,4 thiadiazolyl and tetrazolyl.

Examples of 6-membered monocyclic heteroaryl groups are pyridinyl, pyridazinyl, pyrimidinyl, pyrazinyl, 1,3,5 triazinyl, 1,2,4 triazinyl and 1,2,3 triazinyl.

In one embodiment, 6-membered monocyclic heteroaryl groups contain 1 or 2 ring members which are =N— atoms (where the remainder of the 6 ring members are carbon atoms).

Bicyclic heteroaromatic groups include fused-ring heteroaromatic groups containing 9-13 ring members and 1, 2, 3, 4 or more heteroatoms selected from O, S, N or $NR^N$.

In one embodiment, 9-membered bicyclic heteroaryl groups contain 1 ring member which is an —$NR^N$— group, an —O— atom or an —S— atom and, optionally, 1-3 ring members (e.g. 1 or 2 ring members) which are =N— atoms (where the remainder of the 9 ring members are carbon atoms).

Examples of 9-membered fused-ring bicyclic heteroaryl groups are benzofuranyl, benzothiophenyl, indolyl, benzimidazolyl, indazolyl, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-b]pyridinyl, isoindolyl, indazolyl, purinyl, indolininyl, imidazo[1,2-a]pyridinyl, imidazo[1,5-a]pyridinyl, pyrazolo[1,2-a]pyridinyl, pyrrolo[1,2-b]pyridazinyl and imidazo[1,2-c]pyrimidinyl.

In one embodiment, 10-membered bicyclic heteroaryl groups contain 1-3 ring members which are =N— atoms (where the remainder of the 10 ring members are carbon atoms).

Examples of 10-membered fused-ring bicyclic heteroaryl groups are quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl and pyrimido[4,5-d]pyrimidinyl.

In some embodiments, a heterocyclyl group may be fused to an aryl or heteroaryl group to form a bicyclic ring system containing 5 to 13 members. Examples of such groups include dihydroisoindolyl, dihydroindolyl, tetrahydroisoquinolinyl, tetrahydroquinolinyl or 2,3-dihydro-pyrrolyl-[2,3-b]pyridine.

Alkoxy

The terms "alkoxy" and "alkyloxy" are used herein to refer to an —O-alkyl group in which alkyl is as described above. Exemplary alkoxy groups include methoxy (—$OCH_3$) and ethoxy (—$OC_2H_5$).

Alkylene

The term "alkylene" is used herein to refer to a divalent -alkyl- group in which alkyl is as defined previously. Exemplary alkylene groups include —$CH_2$—, —$(CH_2)_2$— and —$C(CH_3)HCH_2$—.

Heteroalkylene

The term "heteroalkylene" is used herein to refer to a divalent -heteroalkyl- group in which heteroalkyl is as defined previously.

Alkenylene

The term "alkenylene" is used herein to refer to a divalent -alkenyl- group in which alkenyl is as defined previously. Exemplary alkenylene groups include —CH=CH—, —CH=CHCH$_2$—, and —CH$_2$CH=CH—.

Heteroalkenylene

The term "heteroalkenylene" is used herein to refer to a divalent -heteroalkenyl- group in which heteroalkenyl is as defined previously.

Alkynylene

The term "alkynylene" is used herein to refer to a divalent -alkynyl- group in which -alkynyl- refers to a straight or branched chain hydrocarbon group having from 2 to 12, conveniently 2 to 6, carbon atoms and one carbon-carbon triple bond in the chain. Exemplary alkynylene groups include ethynyl and propargyl.

Heteroalkynylene

The term "heteroalkynylene" is used herein to refer to a divalent -heteroalkynyl- group in which heteroalkynyl is as defined previously.

Arylene

The term "arylene" is used herein to refer to a divalent -aryl- group where aryl is as described above which is linked to two or more other groups. Examples of arylene groups include phenylene.

"Phenylene" means a phenyl- group. Exemplary groups are 1,3-phenylene and 1,4-phenylene.

Heteroarylene

The term "heteroarylene" is used herein to refer to a -heteroaryl- group, where heteroaryl is as described above, which is linked to two or more other groups. Exemplary groups include 2,5-furyl, 2,5-thienyl, 2,4-thiazolyl, 2,5-thiazolyl and 2,6-pyridyl.

Measurement Methods

Tensile Modulus

The Young's modulus of the lens materials were determined using a TA-XT2 Texture Analyser, and the value was obtained by drawing a tangent to the initial linear portion of the stress-strain curve, and dividing the tensile stress by the corresponding strain. Measurements were performed on films of 500 μm thickness prepared from the formulations and cut into 10 mm×50 mm samples.

Equilibrium Water Content

The Equilibrium Water Contents (EWC) of the prototype hydrogel lenses produced according to the present invention were determined by gravimetric means. The wet weight of lenses after equilibration in water at room temperature overnight was first measured. The lenses were then dried in an oven at 70° C. to a constant weight, which was the dry weight. The EWC of the lenses was then calculated as follows.

$$EWC(\text{wt \%}) = [(\text{wet weight} - \text{dry weight})/\text{wet weight}] * 100$$

Oxygen Permeability

The oxygen permeability (in barriers) of prototype lenses produced according to the method of the present invention was determined by the polargraphic method generally described in ISO 9913-1:1996(E).

MODES FOR CARRYING OUT THE INVENTION

The following examples describe the method of the present invention and polymers obtained using the method. These examples are intended to illustrate the invention and are not to be construed as being limitations thereon.

EXAMPLE 1

The Preparation of poly(dimethylsiloxane), monomethacryloxypropyl substituted, [2-(trimethylammoniummethyl) phosphate, inner salt]-3'-oxypropyl terminated (SIMA-PC) (m+n≈5; avg. M≈990 g/mol)

The reactions carried out in Example 1 are summarised in scheme 1 below:

SCHEME 1

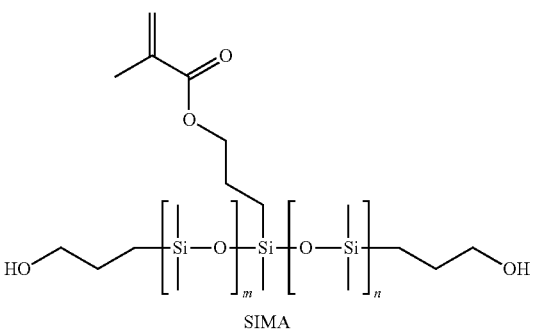

SIMA

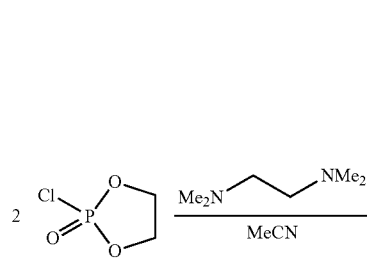
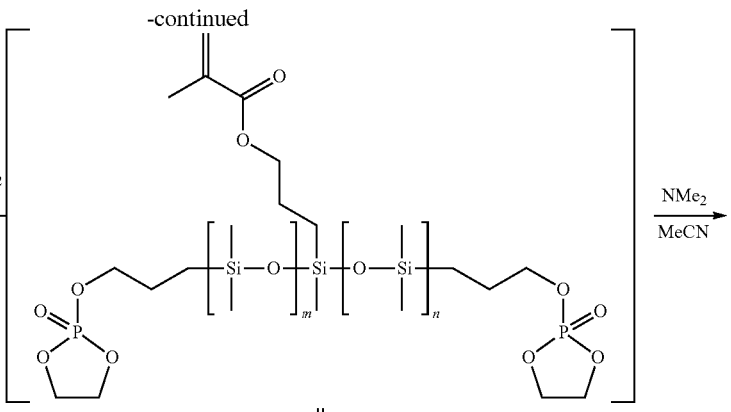
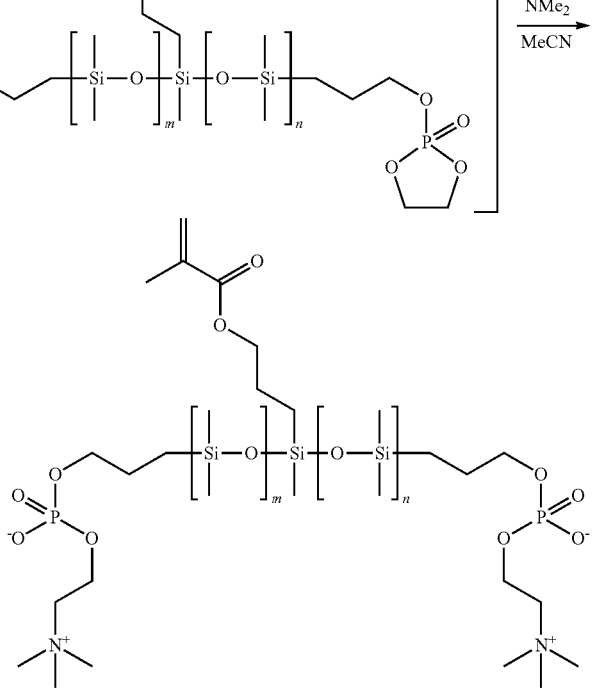

SIMA-PC

To a stirred and chilled (−10° C.) solution of 2-chloro-2-oxo-1,3,2-dioxaphospholane (19.77 g; 139 mmol; 2.0 equiv.) in acetonitrile (24 g) was dropwise added a solution of poly(dimethylsiloxane), monomethacryloxypropyl substituted, hydroxypropyl terminated (SIMA) (45.80 g; avg. M≈660 g/mol; 69.4 mmol) and N,N,N',N'-tetramethylethylenediamine (8.47 g; 72.9 mmol; 1.05 equiv.) in acetonitrile (60 g). Upon completion of the addition the reaction mixture was left stirring for 15 min, filtered under an argon atmosphere and the N,N,N',N'-tetramethylethylenediamine dihydrochloride precipitate washed with dry acetonitrile (90 g) to give a filtrate comprising a solution of the intermediate bis-d ioxaphospholane in acetonitrile.

To the stirred and chilled phospholane solution was added 2,6-di-tert-butyl-4-methylphenol (BHT) (30 mg; 0.136 mmol), acetonitrile (260 g) and trimethylamine (14.4 g; 243 mmol; 3.5 equiv.) and the reaction mixture was heated in a closed system (water condenser fitted with balloon) at 70° C. for 17 h. The reaction mixture was concentrated (ca. 100 mL of acetonitrile and excess trimethylamine removed) under vacuum and the product allowed to crystallise out of solution at around −25° C.

The crystalline product was rapidly filtered under argon atmosphere and dried in vacuo at ambient temperature to afford the target compound (16.30 g; 16.5 mmol; 24%) ($R_f$ (MeOH)=0.02) as a white solid (m.p. 215-220° C.). Average composition: $C_{34}H_{82}N_2O_{15}P_2Si_6$ (avg. M≈989.48 g/mol).

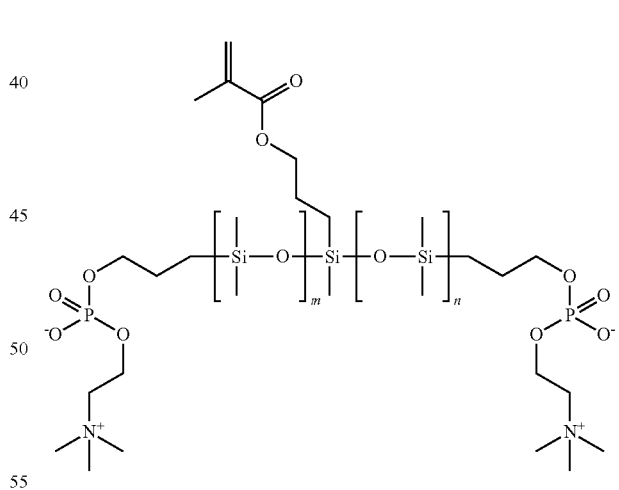

$^1$H-NMR (400 MHz) (CD$_3$OD): δ=6.08 (s, 1H, =CH$_2$), 5.64-5.58 (m, 1H, =CH$_2$), 4.30-4.19 (m, 4H, —OCH$_2$—CH$_2$N$^+$—), 4.14-4.07 (m, 2H, —(C=O)—O—CH$_2$—), 3.84 and 3.82 (2× t like 1× q, 4H, —O—($^-$O—)P(=O)—O—CH$_2$—CH$_2$—CH$_2$—Si—, J=6.7 Hz), 3.67-3.60 (m, 4H, —CH$_2$N$^+$—), 3.25, 3.24 and 3.22 (3× s, 18H, —N$^+$(CH$_3$)$_3$), 1.93 (s, 3H, —C(CH$_3$)=CH$_2$), 1.80-1.61 (m, 6H, —Si—CH$_2$-CH$_2$—), 0.65-0.51 (m, 6H, —Si—CH$_2$—), 0.14-0.04 (m, 33H, —Si—CH$_3$) ppm. $^{31}$P-NMR (162 MHz) (CD$_3$OD): δ=−0.08 ppm.

EXAMPLE 2

The Preparation of (3-methacryloxy-2-[trimethylammoniumethyl]-phosphate, inner salt, propoxy)propyl-bis(trimethylsiloxy)methylsilane The reactions carried out in Example 2 are summarised in scheme 2 below:

Scheme 2

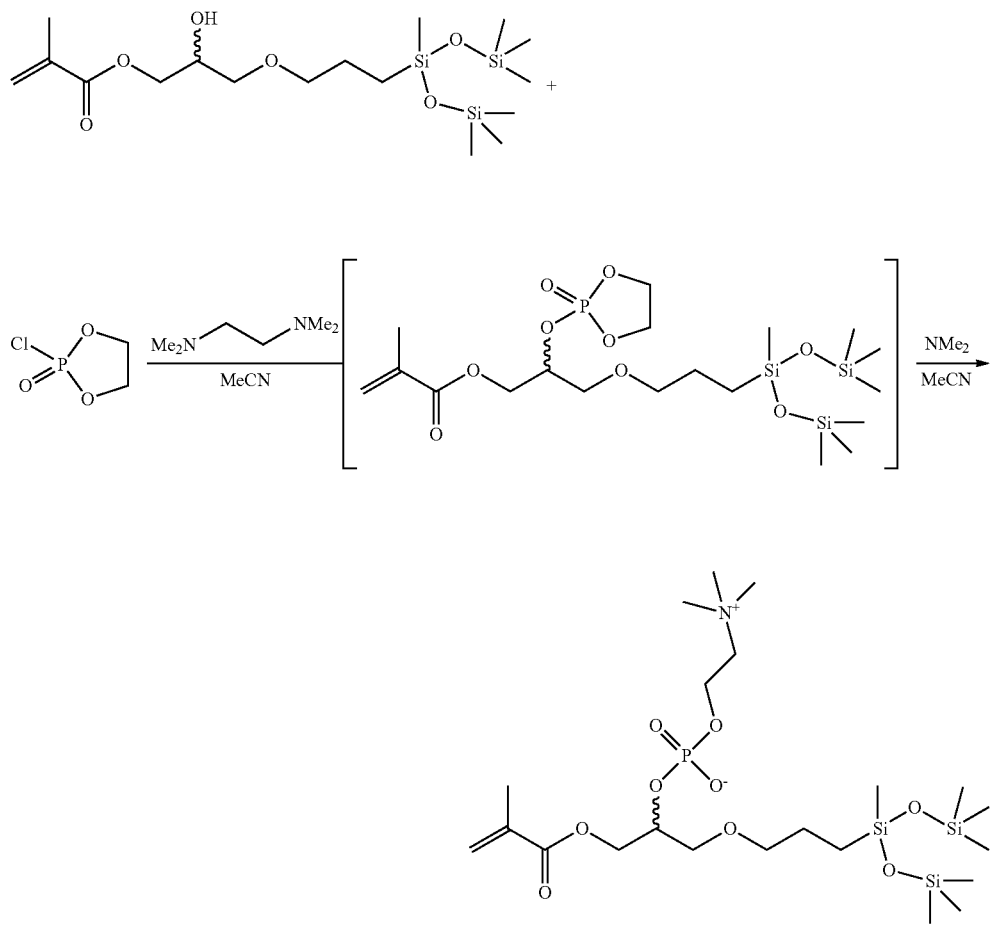

To a stirred and chilled (−10° C.) solution of 2-chloro-2-oxo-1,3,2-dioxaphospholane (2.10 g; 14.8 mmol; 1.25 equiv.) in acetonitrile (1.0 g) was added dropwise a solution of (3-methacryloxy-2-hydroxypropoxy)propyl-bis(trimethylsiloxy)methylsilane (5.00 g; 11.8 mmol) and N,N,N',N'-tetramethylethylenediamine (0.91 g; 7.81 mmol; 0.66 equiv.) in acetonitrile (3.0 g). Upon completion of the addition the reaction mixture was left stirring for 17 h, filtered under an argon atmosphere and the precipitate washed with dry acetonitrile (3.0 g) to give a filtrate comprising a solution of the intermediate dioxapholane in acetonitrile.

To the stirred and chilled phospholane solution was added 2,6-di-tert-butyl-4-methylphenol (BHT) (3 mg; 14 μmol), acetonitrile (11 g) and trimethylamine (1.4 g; 23.7 mmol; 2.00 equiv.) and the reaction mixture was heated in a closed system (water condenser fitted with balloon) at 70° C. for 24 h. The reaction mixture was concentrated (ca. 5 mL of acetonitrile and excess trimethylamine removed) under vacuum and the product allowed to crystallise out of solution at around −25° C.

The crude product was recrystallised from acetonitrile (2 ml), rapidly filtered under an argon atmosphere, washed with acetonitrile (1 ml) and ethyl acetate (3×1 ml) and dried in vacuo at ambient temperature to afford the target compound (1.9 g; 3.2 mmol; 27%) as a white solid.

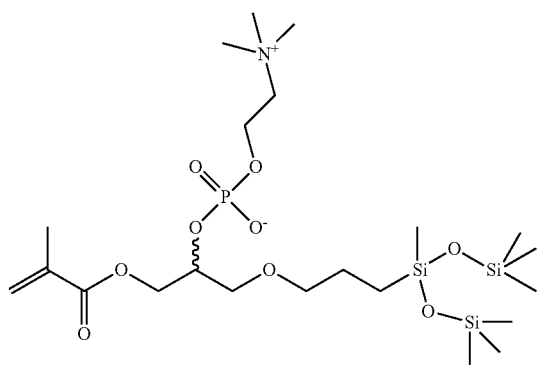

$C_{22}H_{50}NO_9PSi_3$ (M = 587.86 g/mol)

$^1$H-NMR (400 MHz) (CD$_3$OD): δ=6.14 (s, 1H, =CH$_2$), 5.67-5.62 (m, 1H, =CH$_2$), 4.55-4.46 (m, 1H), 4.46-4.39 (m,

1H), 4.35-4.22 (m, 3H, —OCH$_2$—CH$_2$N$^+$— and 1 more H), 4.14-3.99 (m, 1H), 3.70-3.60 (m, 4H, —CH$_2$N$^+$— and 2 more H), 3.45 (t, 2H, —O—CH$_2$—CH$_2$—CH$_2$—Si—, J=6.9 Hz), 3.22 (s, 9H, —N$^+$(CH$_3$)$_3$), 1.95 (s, 3H, —C(CH$_3$)=CH$_2$), 1.66-1.52 (m, 2H, —CH$_2$—CH$_2$—Si—), 0.52-0.43 (m, 2H, —CH$_2$—Si—), 0.10 (2' s, 18H, —Si(CH$_3$)$_3$), 0.04-0.00 (m, 3H, —Si(CH$_3$)(OMe$_3$)$_2$ ppm. $^{31}$P-NMR (162 MHz) (CD$_3$OD): δ=−1.39, −2.03 ppm.

EXAMPLE 3

Preparation of the homopolymer of poly(dimethylsiloxane), monomethacryloxypropyl substituted, [2-(trimethylammoniumethyl) phosphate, inner salt]-3'-oxypropyl terminated (SIMA-PC)

SIMA-PC monomer and the intiator (azobisisobutyronitrile, AIBN 1% of the monomer weight) were dissolved in ethanol (total monomer concentration 1 mol/L). The mixture was charged to a round bottom flask fitted with a mechanical stirrer, thermometer and a condenser. Argon gas was passed through the mixture for 20 min. The polymerization was carried out at reflux for 3 hours, under an argon atmosphere. After that time an initiator solution (AIBN 0.2% of total monomer weight in 3 ml of ethanol) was added to the solution and the reaction was continued for a further 2 hours. The reaction mixture was cooled down and the resulting polymer was isolated by precipitation into diethyl ether. The polymer was filtered and dried under vacuum at room temperature.

$^1$H-NMR (400 MHz) (CD3OD): δ=4.24 (4H, m), 4.05 (2H, b), 3.81 (4H, m), 3.66 (4H, m), 3.23 (18H, s), 1.65 (6H, m), 1.20 (3H, b) and 0.1 (31H, m) ppm.

EXAMPLE 4

Preparation of the copolymer of poly(dimethylsiloxane), monomethacryloxypropyl substituted, [2-(trimethylammoniumethyl) phosphate, inner salt]-3'-oxypropyl terminated (SIMA-PC) and lauryl methacrylate (1:2)

The desired amounts of PC monomer (1 equiv), lauryl methacrylate (2 equiv.) and the intiator (azobisisobutyronitrile, AIBN, 1% of total monomer weight) were dissolved in ethanol (total monomer concentration 1 mol/L). Argon gas was passed through the mixture for 20 min. Ethanol (10 ml) was charged to a round bottom flask fitted with mechanical stirrer, thermometer, a condenser and a feed inlet and the temperature was raised to reflux using a heated oil bath. The monomers and intiator solution mixture was pumped into the reaction flask over a period of about 2 hours. When all the solution was added, reflux was maintained for a further 1 hour. After that time an initiator solution (AIBN 0.2% of total monomer weight in 3 ml of ethanol) was added to the refluxing solution and the reaction was continued for a further 2 hours. The reaction mixture was cooled down and the resulting polymer was isolated by precipitation into diethyl ether. The polymer was filtered and dried under vacuum at room temperature.

NMR data revealed a mixture of copolymer and unreacted monomer.

$^1$H-NMR (400 MHz) (CD3OD): δ=4.24 (m), 3.94 (m), 3.81 (m), 3.65 (m), 3.23 (s), 1.95 (m), 1.66 (m), 1.29 (m) 0.88 (m) and 0.1 (m) ppm.

EXAMPLE 5

Polymer systems were made using the monomer of example 1 using the following general procedure:

Reaction components indicated in table 1 were mixed, de-gased using argon and heated to 70° C. for 1 hr. to give the cross-linked polymer systems derived from the monomer feedstocks.

TABLE 1

| Formulation | Components (wt %) | | | | |
|---|---|---|---|---|---|
| | SIMA-PC | HEMA | DMA | EGDMA | PD16 |
| LN007/2/270b | 49.36 | 49.36 | 0 | 0.79 | 0.49 |
| LN007/2/276 | 39.51 | 59.21 | 0 | 0.79 | 0.49 |
| LN007/2/278 | 39.47 | 39.47 | 19.78 | 0.79 | 0.49 |
| LN007/2/351 | 14.74 | 83.54 | 0 | 0.74 | 0.98 |

EXAMPLE 6

This example describes the general procedure (Table 2) for preparing polymerisable materials and corresponding contact lenses. Unless otherwise stated, all the materials were used as received.

Each component of the polymerisable system including the monomers, cross linker (EGDMA) and initiator (PD16) was weighed and added to a glass vial. The vials were sealed with a cap and then placed on a roller mixer at room temperature until all components were fully dissolved. After dissolution, the mixture was filtered through a 0.45 micron filter and the solution was de-oxygenated by gently bubbling dry argon gas through the formulation.

Polypropylene contact lens molds were cleaned by rinsing with 20% Decon 90 in water followed by drying in an oven at 70° C. for 30 min. The female molds were filled with the formulation and the male molds were added to the female molds. The molds were then placed in an oven preheated to 70° C. for 1 hour.

After cooling, the molds were immersed in purified water overnight to de-mold the lenses.

TABLE 2

| Description | Procedure |
|---|---|
| 1. Mixing | weigh components used to form the polymerisable solution into a glass vial |
| | seal the vial with a lid |
| | place on a roller-mixer at room temperature until fully dissolved, filter through 0.45 micron membrane and deoxygenate |
| 2. Preparation and filling the molds | rinse the plastic molds with 20% Decon 90 in water |
| | dry the molds in an oven at 70° C. for 30 min |
| | fill the molds with the polymerisable solution and close |
| 3. Polymerization | preheat the oven to 70° C. |
| | place the material-containing molds in the oven for 1 hr and then allow to cool for 30 mins |
| 4. Hydration and Demolding | place the lenses/molds in purified water |
| | open the molds and leave overnight |
| | remove the lenses from the molds |

Polymerisable systems incorporating SIMA-PC, as produced in example 1, which gave an essentially clear hydrogel polymer are detailed in Table 3. The abbreviations and corresponding full names of the components are listed in Table 4.

Table 5 summarises certain of the formulation and polymer properties.

TABLE 3

| Formulation | SIMA-PC | MPC | HEMA | VP | SC1 | EGDMA | PD16 | hydrogel clarity |
|---|---|---|---|---|---|---|---|---|
| LN007/2/277 | 29.61 | 0 | 54.31 | 0 | 14.80 | 0.79 | 0.49 | slightly hazy |
| LN007/2/289 | 14.80 | 0 | 64.21 | 0 | 19.70 | 0.79 | 0.49 | clear |
| LN008/30/60 | 22.24 | 10.24 | 43.90 | 0 | 21.85 | 0.76 | 1.00 | clear |
| LN007/2/333 | 9.83 | 4.91 | 58.97 | 9.83 | 14.74 | 0.74 | 0.98 | clear |
| LN007/2/334 | 9.83 | 4.91 | 63.88 | 9.83 | 9.83 | 0.74 | 0.98 | clear |
| LN007/2/335 | 9.83 | 9.83 | 58.97 | 9.83 | 9.83 | 0.74 | 0.98 | clear |
| LN007/2/372 | 14.74 | 14.74 | 39.31 | 0 | 29.48 | 0.74 | 0.98 | clear |
| LN007/2/347 | 14.74 | 0 | 58.97 | 9.83 | 14.74 | 0.74 | 0.98 | clear |
| LN007/2/348 | 14.74 | 9.83 | 58.97 | 0 | 14.74 | 0.74 | 0.98 | clear |
| LN007/2/389 | 9.71 | 14.57 | 39.69 | 0 | 34.32 | 0.72 | 1.00 | clear |

TABLE 4

| Abbreviation | Full name |
|---|---|
| SIMA-PC | Poly(dimethylsiloxane), monomethacryloxypropyl substituted, di-[2-(trimethylammoniumethyl) phosphate, inner salt]-3'-oxypropyl terminated |
| MPC | 2-Methacryloyloxyethylphosphorylcholine |
| HEMA | 2-Hydroxyethylmethacrylate |
| VP | N-Vinylpyrrolidone |
| DMA | Dimethylacrylamide |
| SC1 | (3-Methacryloxy-2-hydroxypropoxy)propyl-bis(trimethylsiloxy)-methylsilane |
| EGDMA | Ethyleneglycoldimethacrylate |
| PD16 | Bis(tert-butylcyclohexyl) peroxydicarbonate |

TABLE 5

| | Before polymerisation | After polymerisation | After hydration | Physical properties | Water content (%) |
|---|---|---|---|---|---|
| LN007/2/289 | clear | clear | clear | Soft, flexible | 26.79 |
| LN007/2/270b | clear | clear | sl. hazy | Soft, flexible | 35.41 |
| LN007/2/347 | clear | clear | clear | Soft, flexible | 32.81 |
| LN007/2/348 | clear | clear | clear | Soft, flexible | 43.34 |

What is claimed is:

1. A polymerisable material of formula (I) or (II):

$$(X-Y^1)_m-W(Y^2-Z)_n \quad (I)$$

$$[(X)_m-Y^3(Z)_p]_v-W-R^1 \quad (II)$$

wherein

X is a polymerisable group;

$Y^1$ and $Y^2$ are each independently a linker group selected from the group consisting of a bond, $C_{1-12}$ alkylene, $C_{2-12}$ alkenylene, $C_{2-12}$ alkynylene, $C_{3-12}$ cycloalkylene, $C_{3-12}$ cycloalkenylene, $C_{2-12}$ heteroalkenylene, $C_{2-12}$ heteroalkynylene, arylene, heteroarylene, —C(O)—$C_{1-12}$ alkylene, —C(S)—$C_{1-12}$ alkylene, —C(O)O—$C_{1-12}$ alkylene, —C(O)S—$C_{1-12}$ alkylene, —C(O)N($R^M$)—$C_{1-12}$ alkylene, —C(S)—$C_{1-12}$ alkylene, —C(S)O—$C_{1-12}$ alkylene, —C(S)S—$C_{1-12}$ alkylene, —C(S)N($R^M$)—$C_{1-12}$ alkylene, —$(CH_2)_q(OCH_2CH_2)_r$—, and —$(CH_2CH_2O)_r(CH_2)_q$—, wherein $R^M$ is hydrogen or $C_{1-4}$ alkyl, q is an integer from 1 to 10, r is an integer from 1 to 10, wherein one or more carbon atoms in the $C_{1-12}$ alkylene group may be optionally replaced with a heteroatom selected from the group consisting of S and O and the alkylene, alkenylene, alkynylene, cycloalkylene, cycloalkenylene, heteroalkenylene, heteroalkynylene, arylene and heteroarylene groups may be optionally substituted with one or more $R^N$, wherein each $R^N$ is independently selected from the group consisting of —H, —OH, —CN, —$NO_2$, —$CF_3$, —$OCF_3$, —$CO_2H$, —$NH_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—$NH_2$, —S(O)$_2$—NH—($C_1$-$C_{10}$ alkyl), —S(O)$_2$—N($C_1$-$C_{10}$ alkyl)$_2$ and =O;

$Y^3$ is a linker group;

$R^1$ is a $C_{1-12}$ alkyl group, optionally substituted with one or more $R^N$;

W is a siloxane group-containing component;

Z is a zwitterionic group;

m is an integer from 1 to 10;

n is an integer from 1 to 3;

p is an integer from 1 to 3;

v is an integer from 1 to 3:

wherein W is a siloxane group of formula

(IIIA)

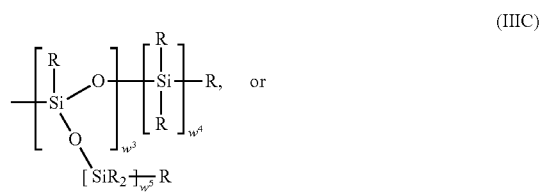

(IIIC)

or

-continued

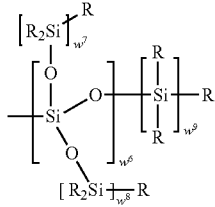

(IIID)

wherein each R is independently selected from hydrogen or a $C_{1-12}$ alkylene, $C_{2-12}$ alkenylene, $C_{2-12}$ alkynylene, $C_{3-12}$ cycloalkylene, $C_{3-12}$ cycloalkenylene, $C_{1-12}$ heteroalkylene, $C_{2-12}$ heteroalkenylene, $C_{2-12}$ heteroalkynylene, arylene, heteroarylene group, optionally substituted with one or more $R^N$, wherein each $R^N$ is independently selected from the group consisting of -H, -OH, -CN, -NO$_2$, -CF$_3$, -OCF$_3$, -CO$_2$H, -NH$_2$, $C_1$-$C_{10}$ alkyl, $C_2$-$C_{10}$ alkenyl, $C_2$-$C_{10}$ alkynyl, -O($C_1$-$C_{10}$ alkyl), -O($C_2$-$C_{10}$ alkenyl), halogen, -C(O)H, -C(O)-($C_1$-10 alkyl), -C(O)-O($C_1$-$C_{10}$ alkyl), -NH($C_1$-$C_{10}$ alkyl), -N($C_1$-$C_{10}$ alkyl)$_2$, -C(O)-NH($C_1$-$C_{10}$ alkyl), -C(O)-N($C_1$-$C_{10}$ alkyl)$_2$, -NH-C(O)-($C_1$-$C_{10}$ alkyl), -NH($C_1$-$C_{10}$ alkyl)-C(O)-($C_1$-$C_{10}$ alkyl), -NH-S(O)$_2$-($C_1$-$C_{10}$ alkyl), -NH-($C_1$-$C_{10}$ alkyl)-S(O)$_2$-($C_1$-$C_{10}$ alkyl), -(C$_0$-$C_{10}$)-SH, -S(O)-($C_1$-$C_{10}$ alkyl), -S(O)$_2$-($C_1$-$C_{10}$ alkyl), -S(O)$_2$-NH$_2$, -S(O)$_2$-NH-($C_1$-$C_{10}$ alkyl), -S(O)$_2$-N($C_1$-$C_{10}$ alkyl)$_2$ and =O; and w, $w^3$, $w^4$, $w^5$, $w^6$, $w^7$, $w^8$, and $w^9$, are each independently an integer in the range from 1 to 500.

2. The polymerisable material of claim 1, wherein X is a polymerisable group selected from the group consisting of acrylates, methacrylates, styrenes, vinyls and multi-functionalised derivatives.

3. The polymerisable material of claim 2, wherein X is a methacrylate group.

4. The polymerisable material of claim 1, wherein $Y^3$ is selected from the group consisting of a bond, $C_{1-12}$ alkylene, $C_{2-12}$ alkenylene, $C_{2-12}$ alkynylene, $C_{3-12}$ cycloalkylene, $C_{3-12}$ cycloalkenylene, $C_{1-12}$ heteroalkylene $C_{2-12}$ heteroalkenylene, $C_{2-12}$ heteroalkynylene, arylene, heteroarylene, —C(O)—$C_{1-12}$ alkylene, —C(S)—$C_{1-12}$ alkylene, —C(O)O—$C_{1-12}$ alkylene, —C(O)S—$C_{1-12}$ alkylene, —C(O)N(R$^M$)—$C_{1-12}$ alkylene, —C(S)—$C_{1-12}$ alkylene, —C(S)O—$C_{1-12}$ alkylene, —C(S)S—$C_{1-12}$ alkylene, —C(S)N(R$^M$)—$C_{1-12}$ alkylene, wherein R$^M$ is hydrogen or $C_{1-4}$ alkyl, wherein the alkylene, alkenylene, alkynylene, cycloalkylene, cycloalkenylene, heteroalkenylene, heteroalkynylene, arylene and heteroarylene groups may be optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —(C$_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O.

5. The polymerisable material of claim 4, wherein the monomer is of formula (II) and wherein $Y^3$ is $C_{1-12}$ heteroalkylene.

6. The polymerisable material of claim 5, wherein the monomer is of formula (II) and wherein $Y^3$ is —(CH$_2$)$_3$—O—(CH$_2$)$_3$—.

7. The polymerisable material of claim 1, wherein the monomer is of formula (I) and wherein $Y^1$ and $Y^2$ are both $C_{1-12}$ alkylene, wherein one or more carbon atoms of the alkylene group have been replaced with a heteroatom selected from the group consisting of O and S.

8. The polymerisable material of claim 1, wherein $Y^1$ is -(CH$_2$CH$_2$O)$_r$-(CH$_2$)$_3$- and $Y^2$ is -(CH$_2$)$_3$(CH$_2$CH$_2$O)$_r$-, wherein r is an integer in the range from 1 to 10.

9. The polymerisable material of claim 1, wherein W is a siloxane group of formula (IIIA):

(IIIA)

wherein each R is independently selected from hydrogen or a $C_{1-12}$ alkylene, $C_{2-12}$ alkenylene, $C_{2-12}$ alkynylene, $C_{3-12}$ cycloalkylene, $C_{3-12}$ cycloalkenylene, $C_{1-12}$ heteroalkylene, $C_{2-12}$ heteroalkenylene, $C_{2-12}$ heteroalkynylene, arylene, heteroarylene group, optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{13}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —(C$_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O and w is an integer from 1 to 500.

10. The polymerisable material of claim 1, wherein W is a siloxane group of formula (IIIC):

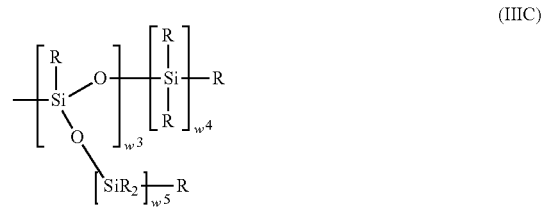

(IIIC)

wherein each R is independently selected from hydrogen or a $C_{1-12}$ alkylene, $C_{2-12}$ alkenylene, $C_{2-12}$ alkynylene, $C_{3-12}$ cycloalkylene, $C_{3-12}$ cycloalkenylene, $C_{1-12}$ heteroalkylene, $C_{2-12}$ heteroalkenylene, $C_{2-12}$ heteroalkynylene, arylene, heteroarylene group, optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O and $w^3$, $w^4$ and $w^5$ are each independently an integer in the range from 1 to 500.

11. The polymerisable material of claim 1, wherein W is a siloxane group of formula (IIID):

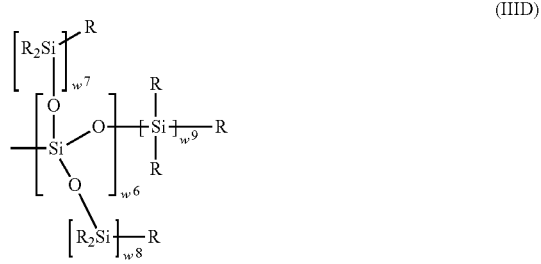

(IIID)

wherein each R is independently selected from hydrogen or a $C_{1-12}$ alkylene, $C_{2-12}$ alkenylene, $C_{2-12}$ alkynylene, $C_{3-12}$ cycloalkylene, $C_{3-12}$ cycloalkenylene, $C_{1-12}$ heteroalkylene, $C_{2-12}$ heteroalkenylene, $C_{2-12}$ heteroalkynylene, arylene, heteroarylene group, optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$alkyl)-C(O)—($C_1$-$C_{10}$ alkyl), —NH—S(O)$_2$—($C_1$-$C_{10}$alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O and $w^6$, $w^7$, $w^8$ and $w^9$ are each independently an integer in the range from 1 to 500.

12. The polymerisable material of claim 1, wherein Z is a zwitterionic group selected from the group consisting of (IVA), (IVB), (IVC), (IVD) and (IVE), wherein group (IVA) has the formula:

(IVA)

wherein each $R^3$ and $R^{3A}$ is independently selected from hydrogen and $C_{1-4}$ alkyl and a is an integer from 2 to 4;

group (IVB) has the formula:

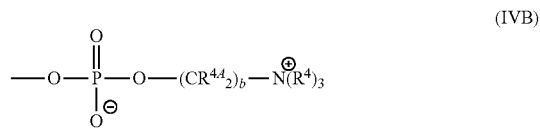

(IVB)

wherein each $R^4$ and $R^{4A}$ is independently selected from hydrogen and $C_{1-4}$ alkyl and b is an integer from 1 to 4;

group (IVC) has the formula:

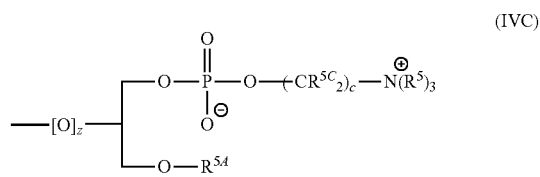

(IVC)

wherein each $R^5$ and $R^{5C}$ is independently selected from hydrogen and $C_{1-4}$ alkyl; $R^{5A}$ is hydrogen or a group —C(O)B$^1$R$^{5B}$, wherein R$^{5B}$ is hydrogen or methyl, B$^1$ is selected from the group consisting of a bond; $C_{1-10}$ alkylene, $C_{2-10}$ alkenylene, $C_{2-10}$ alkynylene, $C_{3-10}$ cycloalkylene, $C_{3-10}$ cycloalkenylene, $C_{1-10}$ heteroalkylene, $C_{2-10}$ heteroalkenylene, $C_{2-10}$ heteroalkynylene, arylene, heteroarylene, —C(O)R$^M$—, —C(O)OR$^M$—, wherein R$^M$ is selected from the group consisting of $C_{1-10}$ alkylene, $C_{2-10}$ alkenylene and $C_{2-10}$ alkynylene, and wherein the alkylene, alkenylene, alkynylene, cycloalkylene, cycloalkenylene, heteroalkylene, heteroalkenylene, heteroalkynylene, arylene and heteroarylene groups may be optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O, and c is an integer from 1 to 4, wherein if Z is directly bonded to an O or N atom, z is 0 and otherwise z is 1;

group (IVD) has the formula:

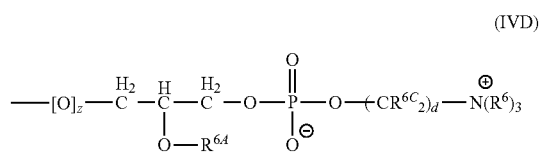

(IVD)

wherein each $R^6$ and $R^{6C}$ is independently selected from hydrogen and $C_{1-4}$ alkyl; $R^{6A}$ is hydrogen or a group —C(O)$B^2R^{6B}$, wherein $R^{6B}$ is hydrogen or methyl, $B^2$ is selected from the group consisting of a bond; $C_{1-10}$ alkylene, $C_{2-10}$ alkenylene, $C_{2-10}$ alkynylene, $C_{3-10}$ cycloalkylene, $C_{3-10}$ cycloalkenylene, $C_{1-10}$ heteroalkylene, $C_{2-10}$ heteroalkenylene, $C_{2-10}$ heteroalkynylene, arylene, heteroarylene, —C(O)$R^M$—, —C(O)O$R^M$—, wherein $R^M$ is selected from the group consisting of $C_{1-10}$ alkylene, $C_{2-10}$ alkenylene and $C_{2-10}$ alkynylene, and wherein the alkylene, alkenylene, alkynylene, cycloalkylene, cycloalkenylene, heteroalkylene, heteroalkenylene, heteroalkynylene, arylene and heteroarylene groups may be optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O, and d is an integer from 1 to 4, wherein if Z is directly bonded to an O or N atom, z is 0 and otherwise z is 1;

group (IVE) has the formula:

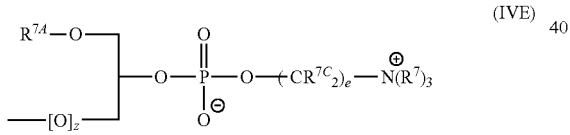

(IVE)

wherein each $R^7$ and $R^{7C}$ is independently selected from hydrogen and $C_{1-4}$ alkyl; $R^{7A}$ is hydrogen or a group —C(O)$B^2R^{7B}$, wherein $R^{7B}$ is hydrogen or methyl, $B^2$ is selected from the group consisting of a bond; $C_{1-10}$ alkylene, $C_{2-10}$ alkenylene, $C_{2-10}$ alkynylene, $C_{3-10}$ cycloalkylene, $C_{3-10}$ cycloalkenylene, $C_{1-10}$ heteroalkylene, $C_{2-10}$ heteroalkenylene, $C_{2-10}$ heteroalkynylene, arylene, heteroarylene, —C(O)$R^M$—, —C(O)O$R^M$—, wherein $R^M$ is selected from the group consisting of $C_{1-10}$ alkylene, $C_{2-10}$ alkenylene and $C_{2-10}$ alkynylene, and wherein the alkylene, alkenylene, alkynylene, cycloalkylene, cycloalkenylene, heteroalkylene, heteroalkenylene, heteroalkynylene, arylene and heteroarylene groups may be optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O, and e is an integer from 1 to 4, wherein if Z is directly bonded to an O or N atom, z is 0 and otherwise z is 1.

13. The polymerisable material of claim 12, wherein Z is a zwitterionic group of formula (IVB).

14. The polymerisable material of claim 13, wherein $R^4$ is methyl and b is 2.

15. The polymerisable material of claim 1 of formula (II), having the structure:

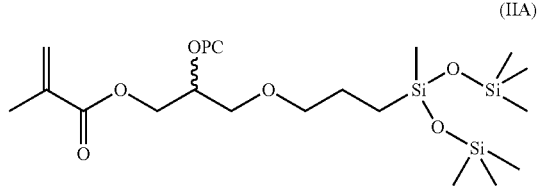

(IIA)

wherein "OPC" is a zwitterionic group of formula (IVB),

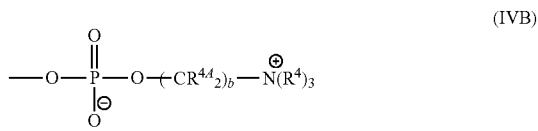

(IVB)

wherein each $R^{4A}$ is independently selected from hydrogen and $C_{1-4}$ alkyl; all $R^4$ groups are methyl; and b is 2.

16. The polymerisable material of claim 1 of formula (II), having the structure:

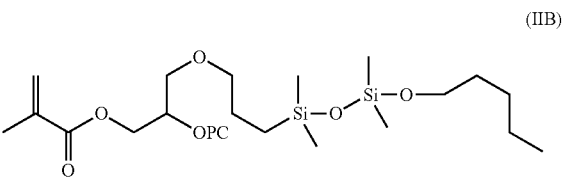

(IIB)

wherein "OPC" is a zwitterionic group of formula (IVB), wherein all $R^4$ groups are methyl and b is 2. Wherein "OPC" is a zwitterionic group of formula (IVB),

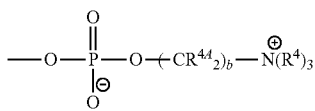

(IVB)

wherein each $R^{4A}$ is independently selected from hydrogen and $C_{1-14}$ alkyl; all $R^4$ groups are methyl; and b is 2.

17. The polymerisable material of claim 1 of formula (II), having the structure:

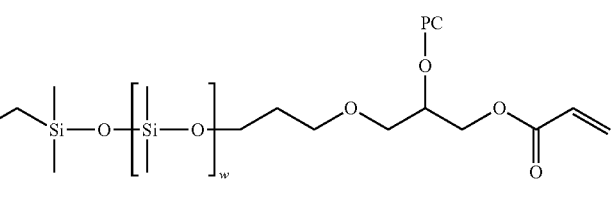

(IIC)

wherein "OPC" is a zwitterionic group of formula (IVB),

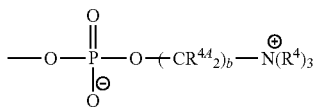

(IVB)

wherein each $R^{4A}$ is independently selected from hydrogen and $C_{1-4}$ alkyl; all $R^4$ groups are methyl; b is 2, and w is an integer from 1 to 500.

18. A method for producing a polymer comprising polymerising the polymerisable material of claim 1.

19. A polymer obtained by polymerising the polymerisable material of claim 1.

20. A xerogel comprising the polymer of claim 19, which is free from water.

21. A silicone hydrogel comprising the polymer of claim 19, and water in an amount of 30 to 80% by weight of hydrogel.

22. The polymer of claim 19, which has an equilibrium water content in the range from 30 to 50%.

23. The polymer of claim 19, which has a modulus in the range from 0.5 to 1.0 MPa.

24. An article comprising the polymer of claim 19.

25. The article of claim 24, which is a contact lens.

26. The contact lens of claim 25, which has an oxygen permeability of about 30 barriers or more.

27. The contact lens of claim 25, which has an equilibrium water content in the range from 30 to 50%.

28. An article comprising a surface having coated thereon the polymer of claim 19.

29. The article of claim 28, which is a contact lens.

30. A method of coating an article having a surface comprising applying the polymer of claim 19 to the surface of the article.

31. A polymerisable material having the structure:

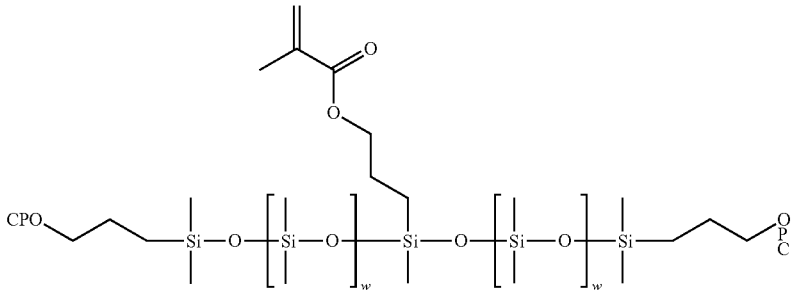

wherein "OPC" is a zwitterionic group of formula (IVB),

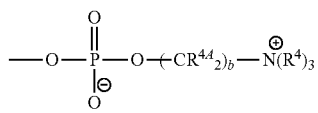

(IVB)

wherein each $R^{4A}$ is independently selected from hydrogen and $C_{1-4}$ alkyl; all $R^4$ groups are methyl; b is 2; and w is from 0 to 15.

* * * * *

UNITED STATES PATENT AND TRADEMARK OFFICE
CERTIFICATE OF CORRECTION

PATENT NO. : 8,980,972 B2
APPLICATION NO. : 13/601211
DATED : March 17, 2015
INVENTOR(S) : Michael Driver et al.

It is certified that error appears in the above-identified patent and that said Letters Patent is hereby corrected as shown below:

IN THE CLAIMS

In Claim 1, Col. 39, Line 22, immediately after "-O($C_2$-$C_{10}$ alkenyl)," and immediately before "halogen," please insert -- -O($C_2$-$C_{10}$ alkynyl), --.

In Claim 1, Col. 39, Line 23, immediately after "-C(O)H," and immediately before "-C(O)-O($C_1$-$C_{10}$ alkyl)," please delete "-C(O) -($C_1$-10 alkyl)," and insert -- -C(O)-($C_1$-$C_{10}$ alkyl), -- therefor.

In Claim 1, Col. 39, Line 31, immediately after "$w^7$, $w^8$," and immediately before "each independently," please delete "and $w^9$, are" and insert -- and $w^9$ are -- therefor.

In Claim 9, Col. 40, Line 31, immediately after "-O($C_1$-$C_{10}$ alkyl)," and immediately before "-O($C_2$-$C_{10}$ alkynyl)," please delete "-O($C_2$-$C_{13}$ alkenyl)," and insert -- -O($C_2$-$C_{10}$ alkenyl), -- therefor.

In Claim 31, Col. 46, Line 34, immediately after "the structure:" and immediately before "wherein "OPC"" please delete "

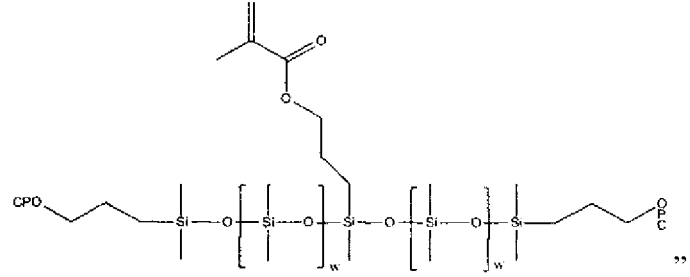

"

and insert --

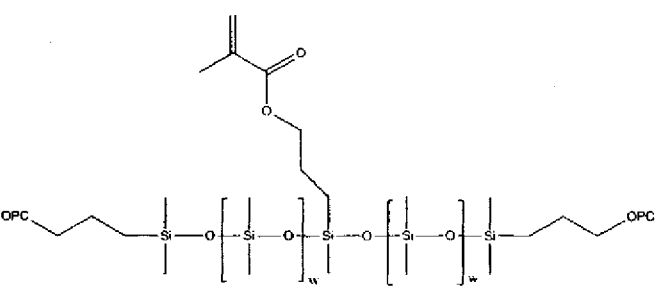

-- therefor.

Signed and Sealed this
Twenty-third Day of February, 2016

Michelle K. Lee
*Director of the United States Patent and Trademark Office*